x

US007166640B2

(12) United States Patent
Berg

(10) Patent No.: US 7,166,640 B2
(45) Date of Patent: Jan. 23, 2007

(54) METHOD OF TREATING SYMPTOMS OF COMMON COLD, ALLERGIC RHINITIS AND INFECTIONS RELATING TO THE RESPIRATORY TRACT

(75) Inventor: Kurt Frimman Berg, Charlottenlund (DK)

(73) Assignee: Immupharm APS, Aalborg (DK)

( * ) Notice: Subject to any disclaimer, the term of this patent is extended or adjusted under 35 U.S.C. 154(b) by 0 days.

(21) Appl. No.: 10/363,430

(22) PCT Filed: Jul. 23, 2001

(86) PCT No.: PCT/DK01/00515

§ 371 (c)(1),
(2), (4) Date: Sep. 22, 2003

(87) PCT Pub. No.: WO02/09699

PCT Pub. Date: Feb. 7, 2002

(65) Prior Publication Data

US 2004/0053858 A1     Mar. 18, 2004

(30) Foreign Application Priority Data

| Jul. 28, 2000 | (DK) | ............................ | 2000 01152 |
| Sep. 4, 2000 | (DK) | ............................ | 2000 01316 |
| Dec. 23, 2000 | (DK) | ............................ | 2000 01935 |
| Jan. 30, 2001 | (DK) | ............................ | 2001 00007 |
| May 22, 2001 | (DK) | ............................ | 2001 00827 |

(51) Int. Cl.
*A61K 31/35* (2006.01)
*A01N 43/16* (2006.01)

(52) U.S. Cl. .................................... 514/456
(58) Field of Classification Search ................. 514/456
See application file for complete search history.

(56) References Cited

U.S. PATENT DOCUMENTS

| 3,516,984 A | * | 6/1970 | Courbat .......................... 536/8 |
| 4,888,326 A | * | 12/1989 | Horrobin ...................... 514/27 |
| 4,956,385 A | * | 9/1990 | Eby, III ....................... 514/494 |

FOREIGN PATENT DOCUMENTS

WO          02076422          10/2002

OTHER PUBLICATIONS

Rink and Kirchner, Journal of Nutrition. 2000;130:1407S-1411S, the content of the paper has been presented in Nov. 1998.*
Bardsley-Elliot, Drugs, 1999;58(5):851-860.*
"The Merck Manual of Diagnosis and Therapy", Merck Research Laboratories, Seventeenth Edition, Whitehouse Station, N.J., pp. 556-569, chapter 68, section 6, 1999.

Michael Hermann Hinz, Neuartige Wirkoffkomination von bioligisch hochwirksamen Flouriden u. Flavonoiden zur Therapie und Prphylaxe von Zahnerkrankungen. DE 19949575 Apr. 19, 2001, ISR Sep. 13, 2002.
Andreas Vincze, Hans-Jürgen Reimann, Pharmazeutische Zubereitung, die als aktive Substanz eine Mischung von (+) Catechin und ascorbolysinat enthält, DE 3603227 Aug. 8, 1987, ISR Sep. 13, 2002.
Ismail Roshdy, Vitamin E-haltiges Mittel zur verbesserung der Eigenschaften des Blutes, EP 0204987 Dec. 17, 1986, ISR Sep. 13, 2002.
Yin Hwee Tan, Use of fatty acids for the treatment of diseases associated with cytokines. EP 0396251 Nov. 7, 1990.
Tadakatsu Shimamura, Yukihiko Hara, Preventive and curative midicament against infection with influenza virus, containing tea or tea polyphenols. EP 0417385 Mar. 20, 1991, ISR Sep. 13, 2002.
Joseph A. Deihl, Vitamin-mineral treatment methods and compositions, EP 0754450 Jan. 22, 1997, ISR Sep. 13, 2002.
Thomas Coleman, Nasal spray for treating viral common colds. EP 0861662 Sep. 2, 1998, ISR Sep. 13, 2002.
Kayano Masako, Yazawa Toshiya, Shigeta Shiro, Baba Masanori, Anti-RS virus agent, JP 04368331 Dec. 21, 1992.
M. Kumai, Cold-preventing troche used orally to inhibit virus—consist of layered structure contg. Catechin, lysozyme, vitamin=C and puerariae radix. JP 08239319.
Shiba Kozaburo, Fanctional japanese apricot chocolate, JP 09056333 Mar. 4, 1997.
Nakayama Mikio, Chewing gum and its production, JP 10257856 Sep. 29, 1998, ISR Sep. 13, 2002.
Kitasato Kenkyusho, Anti-influenza virus agent—contains flavonoid(s) and cellulose ether(s). JP 09227373.
Tsunoda Kenji, Nasal composition, JP 10110785 Nov. 2, 1999, ISR Sep. 13, 2002.
Fukuda Shigeatsu, Composition, JP 11100325, Apr. 4, 1999, ISR Sep. 13, 2002.
Kitajima Hideaki, Okudaira Ichiro, Tsunoda Kenji, Nasal composition, JP 11302184 Nov. 2, 1999.
Taisho Pharm Co. Ltd, Composition for mocous membranes for alleviating symptoms caused by excessive promotion of secretory glands e.g. pollen allergy, comprises a polyphenol. JP 2000327573.
Pierre J. Courbat, Abstract of the disclosure, US 3420815 Jan. 7, 1969.
John R. Casley-Smith, Treatment of high protein oedemas, US 5096887 Mar. 17, 1992, ISR Sep. 13, 2002.
Quing Non Yng-Wong, Antiviral and antimicrobial herbal complex, US 5834000 Nov. 10, 1998.

(Continued)

*Primary Examiner*—San-Ming Hui
(74) *Attorney, Agent, or Firm*—Iver P. Cooper

(57) ABSTRACT

The present invention relates to methods of treating conditions and/or symptoms related to common cold of the upper and/or lower respiratory tract and/or eyes. In particular the invention relates to the methods of treating conditions and/or symptoms related to common cold comprising administration of a flavonoid or administration of a flavonoid in combination with a metal. The invention furthermore describes compositions comprising a metal and a flavonoid useful for the treatment of conditions and/or symptoms relates to common cold.

30 Claims, 7 Drawing Sheets

OTHER PUBLICATIONS

Figure 1:
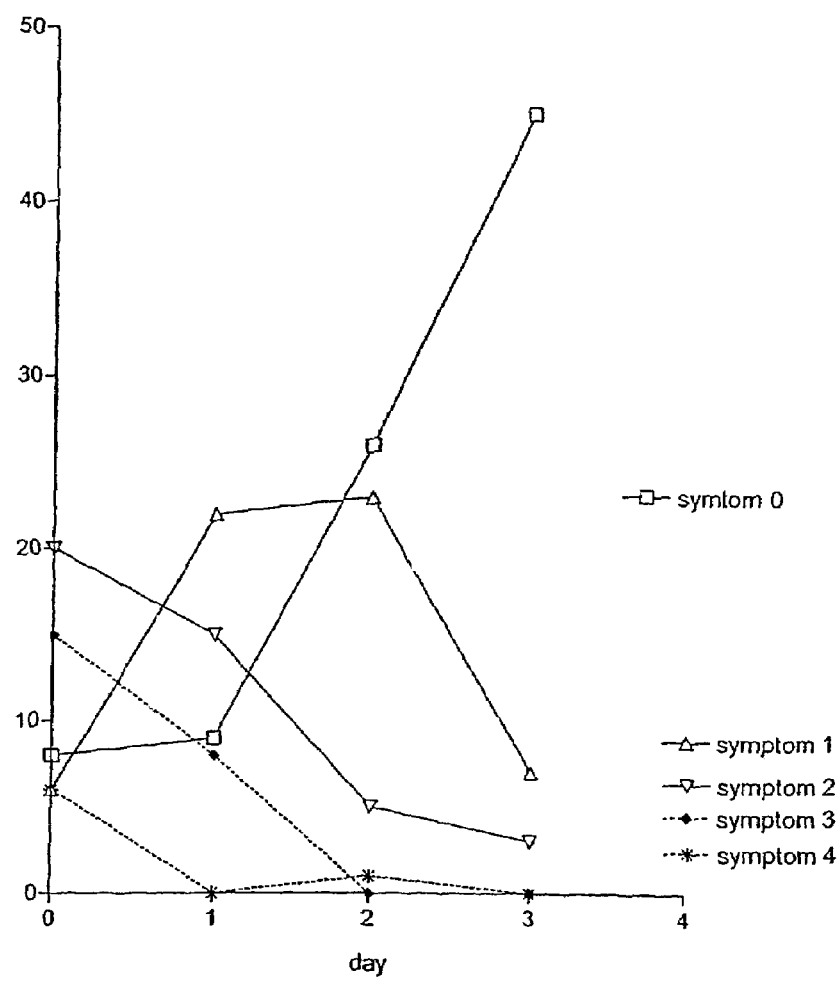

Kazuo Nashimoto, Yoshikazu Tashiro, Gargling cup, antiviral mask, antiviral filter, antifungal, antibacterial, and antiviral filter air-cleaner humidifier, US 5888527 Mar. 30, 1999, ISR Sep. 13, 2002.

Marion Man-Ying Chan, Method of inhibiting nitric oxide synthase, US 5922756 Jul. 13, 1999, ISR Sep. 13, 2002.

Masayoshi Yamaguchi, Composition for stimulating osteogenesis and preventingreduction of bone salt. US 5935996 Aug. 10, 1999, ISR Sep. 13, 2002.

Shibuya, Takashi, Ario, Takeshi, Fukuda, Shigeharu, Composition, US 6224872 May 1, 2001, ISR Sep. 13, 2002.

R. T. Jordan, L. M. Allen, Lipoxygenase inhibitors, WO 88/03800 Jun. 2, 1988, ISR Sep. 13, 2002.

R. T. Jordan, L. M. Allen, Pharmacologically active compounds and mixtures thereof, organic compositions and metal salts. WO 88/03805 Jun. 2, 1988, ISR Sep. 13, 2002.

K. A. Jacobson, J. Jiang, Y. Karton, A. M. Van Rhee, Dihydropyridine-, pyridine-, benzopyran-, one- and trizoloquinazoline derivative, their preparation and their use as adenosine receptor antagonists. WO 97/27177 Jul. 31, 1997, ISR Sep. 13, 2002.

D. P. Jones, S. Furukawa, Compounds and their combinations for the treatment of influenza infection. WO 98/30228 Jul. 16, 1998, ISR Sep. 13, 2002.

F. Stanislaus, Stabilized medicaments containing cysteinyl derivatives, WO 98/47534, Oct. 29, 1998, ISR Sep. 13, 2002.

Weider Nutrition International, INC. Compositions and treatments to reduce side effects of administration of androgenic testoterone precursors. WO 99/07381 Feb. 18, 1999, ISR Sep. 13, 2002.

P. Han, Q. Guo, A *fagopyrum cymosum* (trev.) meisn composition, method to prepare and analyze the same and uses thereof. WO99/16319 Apr. 8, 1999, ISR Sep. 13, 2002.

M. Heng, Method for using soluble curcumin to inhibit phosphorylase kinase in inflammatory diseases. WO 00/70949 Nov. 30, 2000.

P. T. Prendergast, Use of flavones, coumarins and related compounds to treat infections. WO 01/03681 Jan. 18, 2001.

L. Kurppa, Flavonoid drug and dosage form, its production and use. WO 01/49285 Jul. 12, 2001.

M. H. Beers, M. d. berkow, The Merch manual of diagnosis and therapy, p. 1277-1293, 1999 Merck Research, ISR Sep. 13, 2002.

J. V. Formica, W. Regelson, Review of the biology of quercetin and related bioflavonoids. Fd Chem. Toxic. vol. 33, No. 12, pp. 1061-1080, 1995.

J. E. F. Reynolds, Martindale- the extra phamacopoeia, thirty-first edition, pp. 1679-1680, 1996, ISR Sep. 13, 2002.

K. Parfitt, Matindale—The complete drug reference . . . pp. 1373-1374, ISR Sep. 13, 2002.

Tej N. Kaul, Elliot Middleton Jr., Pearay L. Ogra. Antiviral effect of flavonoids on human viruses, Journal of Medical Virology 15:71-79, 1985.

S. B. Mossad, M. L. Macknin, S. V. Medendorph, P. Mason, Zinc gluconate lozenges for treating the common cold, Annals of internal medicine, vol. 125, p. 81-88, 1996.

I.M. Selivanova, N.A. Tyukavkina, Yu.A. Kolesnik, V.K. Kolkhir, V.Lyubimov, Investigation of absorption of diquertin in vitro gastrointestinal model, Farmatsiya, 47:27-28, 1998.

M. Tordea, M. L. Ferrándiz, M. J. Alcaraz, Influence of anti-inflammatory flavonoids on degranulation and arachidonic acid release in rat neutrophils, Z. Naturforsch, vol. 49, p. 235-240, 1993.

Baumann, et al., "Flavonoids and Related Compounds as Inhibitors of Arachidonic Acid Peroxidation", *Prostaglandins*, Jul. 1980.

* cited by examiner

Day 0: the status of the patient at the first visit at the doctor.
Day 1: 24 h after the 1st visit
Day 2: 48 h after the 1st. visit
Day 3: 72 h after the 1st. visit

METHOD OF TREATING SYMPTOMS OF COMMON COLD, ALLERGIC RHINITIS AND INFECTIONS RELATING TO THE RESPIRATORY TRACT

FIELD OF THE INVENTION

The present invention relates to the use of a therapeutically effective amount of a flavonoid and/or a flavonoid derivative such as for example troxerutin or Veneruton® and/or a pharmaceutically acceptable salt thereof, together with a pharmaceutically acceptable carrier for the preparation of a medicament for treatment of one or more conditions related to common cold of the upper and/or lower respiratory tract and/or eyes. Such conditions comprises "common cold", a virus infection or bacterial infection related to the syndrome of common cold, an allergic condition having one or more symptoms similar with the symptoms of a common cold for example allergic rhinitis initiated by rhinovirus infection, asthma like exacerbations and/or other abnormal airway functions derived from Various dysfunctions of the immune system, such as for example hay fever or the like.

The present invention further relates to a medicament for prevention and/or treatment of infections and optionally inflammations accompanying infections of the respiratory tract initiated by microorganisms. The invention relates more specifically to a medicament comprising a flavonoid and/or a flavonoid derivative, for example Venoruton® or Troxerutin, as the active substance in said medicament.

The present invention further relates to a medicament comprising zinc and a flavonoid for the treatment of conditions relating to common cold and/or symptoms relating to common cold, as well as to a method of treatment of conditions relating to common cold or symptoms relating to common cold involving administration of zinc and a flavonoid.

BACKGROUND ART

In the prior art no fast working and efficient composition has been provided for preventing and/or treating common colds initiated by viral infections caused by the so-called cold viruses, such as rhino virus, corona virus, adenovirus, coxsackie virus, RS-virus, echovirus or other cold viruses yielding the usual well known cold syndromes in patients. Practically all humans suffer 2 to 3 times a year from infections in the upper respiratory passages, such as cold and flu. In general, in Denmark the majority of common colds occurring in September, October and November are caused by rhinovirus infection, whereas the majority of common cold occurring in January, February and March are caused by Coronavirus infections.

Furthermore, there is a great deed for effective remedies in the increasing number of patients suffering from allergic syndromes, for example asthma, which may be initiated by common cold viruses, especially the rhinovirus.

Recent observations from a polymerase chain reaction (PCR)-study (Johnston, 1993) with naturally rhinovirus infected persons indicates that the actual range for rhinovirus infections involved in common cold syndrome probably is at least twofold higher, compared to findings obtained via the traditional cell culture techniques (40%). This indicates that up to 70–75% of all patients suffering from common colds have a rhinovirus infections ongoing either as a single infection or co-infection (Spector, 1995).

It has been estimated that the average pre-school child experiences 6–10 upper respiratory infections or common colds per year whereas the average adult experiences 2–4 (Sperber, 1989). The effects of the common cold can be uncommonly disruptive, forcing otherwise normal persons to miss work, school, etc. Individuals who are at increased risks, such as individuals suffering from bronchitis or asthma, may also experience a life-threatening exacerbation of their underlying conditions. The average annual expenditure for various cold treatments exceeds USD 2 billion in the United States, alone (Spector, 1995); in the EU a similar figure is expected.

Currently, there is no efficient treatment to offer common cold patients. Some offered treatments may even worsen the cold; for example, it has been demonstrated that the administration of aspirin and acetaminophen may have detrimental effects on cold treatment, neutralising antibodies and even increase nasal problem's (Graham, 1990). Oral alpha-agonist may relieve congestions in many individuals and anti-histamines may sometimes be helpful (Spector, 1995) but no real cure is observed. Prevention or treatment with artificial soluble receptors has not been as successful as hoped (Hayden, 1988); several trials treating common cold patients with interferon have been completely. negative (Monto, 1989; Sperber, 1989). Plecarnil® (which recently (March, 2000) was investigated in several trials and which inhibits the binding of the rhinovirus via its attachment site, termed also negatively.

All these trials, which involved treatment of the syndrome common cold were negative, despite the fact that adequate drug concentrations were present in the nose of the treated persons. These results indicate that reversal of the pathogenic events in rhinovirus colds requires more than just the inhibition of viral replication.

Unfortunately, research in development of novel strategies to treat common cold is complicated by the fact human rhinoviruses only have been reported to infect primates successfully and hence no practical animal model has been developed for rhinovirus infections (Rotbart, 2000).

The development of natural and experimentally induced rhinovirus infections in normal persons are initiated by selected events which can be considered to occur sequentially. The steps in the rhinovirus pathogenesis are believed to include viral entry into the outer nose, mucociliary transport of virus to the posterior pharynx, and initiation of infection in ciliated and non-ciliated epithelial cells of the upper airway. Viral replication peaks on average within 48 h of initiation of infection and persists for up to 3 weeks; Infection is followed by activation of several inflammatory mechanisms, which may include release or induction of interleukins, bradykinins, prostaglandins and possibly histamine, including stimulation of parasympathetic reflexes (the cytokines may counteract each other at certain levels resulting in a very complex pathway). The resultant clinical illness is a rhinosinusitis, pharyngitis, and bronchitis, which on average lasts one week (Gwaltney, 1995).

Occasionally, a secondary bacterial or microbial infection may follow subsequently to the viral infection and a sustained and more serious inflammation may result.

Previously, it was believed that the major part of the virus was produced in the upper nose region and excreted (Winther, 1993a). However, subsequent studies, comparing recovery of virus in nasopharyngeal wash specimens, nasal swabs and pharyngeal swabs showed that the nasopharyngeal wash specimens was consistently superior to the other two specimens in yielding virus (Cate, 1964). From a series of in-depth investigations (Winther, 1984a; Winther, 1984b; Winther, 1984c; Turner, 1984; Farr, 1984; Hayden, 1987;

Winther, 1987a; Winther, 1987b; Winther, 1993b; Arruda, 1995; Winther, 1998) it was concluded that:
(i) the virus was first recovered, at the highest concentrations, from the nasopharynx before it could be recovered in the upper nose region (turbinates).
(ii) no evidence for rhinovirus induced damage of the surface ciliary lining of the inferior turbinate was noted which is in agreement with other investigators suggesting that the virus may be transported to the nasopharynx in the overlaying mucus by mucociliary clearence.
(iii) there was a significant increase of the influx of neutrophils in the same area as in (ii)
(iv) infection of the lining of the nasal cavity was not uniform after intranasal inoculation and seemed not to result in any cell damage at all, cf. (ii) above.
(v) the rate of viral shedding in the nasopharynx was high by day 1 (post infection), whereas cold symptoms did not peak until day 3. The symptoms waned during the first week, but rhinovirus was present during the following 3 weeks.
(vi) The increase of neutrophils correlate with the onset of symptoms, including sore throat. The symptoms include oedema-like symptoms which, in turn, may trigger sneezing and coughing.

In summarising the above findings, it should be stressed that the highest concentration of virus can be recovered from the nasopharynx, and virus usually appears on the turbinate(s) one or two days later, despite the fact that virus is innoculated via the nose (in volunteers); no visible damage of the cell lining in the upper airways was ever demonstrated. Furthermore, as "sore throat" usually develops simultaneously with the appearance of virus in the nasopharynx it can be reasoned that "signal molecules" or the like (Van Damme, 1988) will be made by the relatively few rhinovirus cells infected and that these "cytokine-like molecules" subsequently may activate the "lymphatic ring"—which is located just beneath the nasopharynx—leading to the well-known sore throat which in turn triggers a complex pattern of inflammatory reactions, involving an array of different interferons and cytokines the interaction of which is currently under in-depth investigation. Some of these factors, such as for example Il-1, induce fever in patients. Bradykinines per se may be responsible for the sore throat which is frequently associated with common cold.

The fact that interferon is known to be part of the non-specific innate immune response against viral infections in man has lead to several publications as a number of groups have investigated how much interferon is produced locally during viral infections of the upper-airways. One of the earliest and probably most thorough, in vivo, investigations in man was performed by Cate et al. (Cate, 1969) on volunteers (healthy adult males from federal correctional institutions in USA): the authors were able to demonstrate that most of the persons involved, produced interferon (as demonstrated in nasal washings) during common colds at a level which, at least theoretically, should have been enough to block the viral infection, per se. It is tempting to speculate that if no interactions from the numerous inflammatory actions (including oedemas) had taken place, the infected persons might not had experienced a traditional cold at all.

It has been demonstrated in a recent publication, that the immune system also takes "active part" in the spread of the inflammatory actions since experimental evidence supports the notion that rhinovirus may use some of the effector cells from the immune system as a mean for spreading the inflammatory reactions to the lower airways (Gern, 1996) via initiation of local TNF-alpha production; it is tempting to speculate that the allergic rhinitis is initiated via this mechanism as it has been found that the pathogenesis for asthma is linked to local TNF-alpha production (Broide et al. 1992). Several quarters have thus argued that the asthma syndromes are rhinovirus manifestations of post-infectious events triggered by an array of different cytokines in connection with a "switch" between the Th1 vs. Th2 response (Gern, 1999; Winther, 1998; Grünberg, 1999).

Generally speaking, air-way infections or allergic rhinitis and/or asthma may pose a serious health problems as it can be potentially life-threatening for susceptible groups such as elderly people with chronic airway problems or persons suffering from a deficient immunity, such as AIDS-patients, cancer patients etc. Thus, a simple method of treating these symptoms/syndromes (and possibly also the underlying infections would be of immense importance).

Viral and/or other microbial infections are known to initiate a complex inflammatory response (Ginsburg, 1988) from the patient which probably is mediated by several groups of responder cells including the neutrophile granulocytes, which are specifically increased during a cold. The latter represents approximately more than 95% of all the effector cells; each min. about 6–9 millions neutrophiles enter the upper-airways and slowly pass down the interior surfaces encompassing the upper airways; it may be assumed that the neutrophiles, which are able to release very aggressive enzymes and toxic substances upon proper stimulation will keep the bacterial load of the upper-airways to an acceptable level; the small numbers of *S. pyogenes* or *S. aureus* found in nasopharynx, which otherwise is almost sterile, may stimulate the neutrophiles via the so-called super-antigens to a certain degree thereby limiting the numbers of bacteria in said areas. (dynamic equilibrium/symbiosis).

According to Ihrcke and co-workers.(Ihrcke, 1993) the very early steps in a virus infection (or any other abnormality in the cell lining) can be related to the content and metabolism of heparan sulfate proteoglycan (the major proteoglycan associated with intact endothelial cells). The first element of the model derives from the observation that heparan sulfate is released from the intact endothelial lining of blood vessels during the very first step in an inflammatory response initiated by a viral infection. Accordingly; this loss may seriously compromise the vascular integrity and result in a local edema attracting further neutrophiles via the up-regulation of ICAM-1 markers on the endothelial cells increasing the inflammatory response further. Thus, in a separate experiment, activated neutrophiles were able to release 70% of all cell-associated heparan sulfate proteoglycan within one hour via the subsequent release of heparanase. One important function of heparan sulfate is the maintenance of the endothelial cell integrity. Loss of heparan sulfate partially abrogate the barrier properties of the endothelium and contributes to the edema and exudation of plasma proteins that characterise inflammation.

BRIEF DISCLOSURE OF THE INVENTION

According to the present invention, it is believed that the explanation for the therapeutic failure of the said prior art antiviral therapies is, that the viral infections per se trigger inflammatory responses which can not be expected to respond at all to antiviral drugs, per se. The existence of inflammatory events in rhinovirus induced common colds is substantiated by the finding of elevated concentrations of inflammatory mediators, such as bradykinins, IL-8 in the nasal secretion of persons with colds (Proud, 1990, Naclerio, 1988) and the partial reduction of cold symptoms by treatment with selected antiinflammatory drugs that have no antiviral activity (Gaffey, 1988).

Flavonoids are polyphenolic compounds isolated from a wide variety of plants with over 4000 individual compounds known. They comprise a range of $C_{15}$ aromatic compounds and are found in virtually all land-based green plants. According to one theory, upon administration of flavonoids to an individual the flavonoid molecules are build into a part of the outer layer of the endothelial cell layer and thereby cause a reduction in microvascular hyperpermeability and hence a reduction of the migration of granulocytes through the endothelial layer. Accordingly, flavonoids can be used to inhibit oedemas and to downregulate inflammatory reactions.

WO 01/03681 describes the anti-viral effect of a number of flavonoids for the purpose of treatment of infections, in particular viral infections. Although several flavonoids have been shown to comprise an antiviral effect, a number of flavonoids do not comprise any antiviral effects in laboratory tests. Never the less the present invention discloses that such non-antiviral flavonoids surprisingly are very effective in the treatment of common cold.

Hence, it is a first objective of the present invention to use a therapeutically effective dosage of a flavonoid and/or a flavonoid derivative selected from the group comprising hydroxyethylrutosides, troxerutin, Veneruton, genistein, taxifolin, eriodyctol, catechin, epicatechingallate, pharmaceutical acceptable salts thereof and functional derivatives thereof, together with a, pharmaceutically acceptable carrier for the preparation of a medicament for treatment of one or more conditions and/or symptoms of conditions relating to a common cold of the upper and/or lower respiratory tract and/or eyes.

It is a second objective of the present invention to provide a method of treatment of an individual, including a human being, comprising administering to said individual a therapeutically effective dosage of a flavonoid and/or a flavonoid derivative selected from the group comprising hydroxyethylrutosides, troxerutin, Veneruton, genistein, taxifolin, Leriodyctol, catechin, epicatechin, epigallocatechin, epicatechingallate, pharmaceutical acceptable salts thereof and functional derivatives thereof, for prevention and/or treatment of one or more conditions and/or symptoms of conditions relating to a common cold of the upper and/or lower respiratory tract and/or eyes.

Preferably, said flavonoid and/or flavonoid derivative does not comprise antiviral activity when tested in vitro. It is furthermore preferred that said flavonoid is soluble in water. More preferably, said flavonoid is a hydroxyethylrutoside, which does not comprise antiviral activity when tested in vitro. Yet more preferably, said flavonoid and/or flavonoid derivative is selected from the group consisting of troxerutin, Veneruton, pharmaceutical acceptable salts thereof and functional derivatives thereof. Most preferably, said flavonoid and/or flavonoid derivative is selected from the group consisting of troxerutin and Veneruton®. Veneruton® is a registered trademark of NOVARTIS and comprise a mixture of hydroxyethylrutosides, wherein around 50% is troxerutin.

In one especially preferred embodiment of the present invention the flavonoid is troxerutin of the formula:

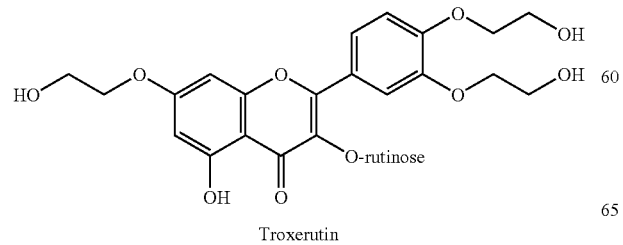

Troxerutin

Even though treatment of common cold patients with zinc gluconate lozenges in one trial performed by Mossad et al. lead to a reduction in the number of days the patients were suffering from common cold symptoms, after 4 days treatment with zinc gluconate lozenges the total symptom score was still more than 50% of the original symptom score. Interestingly, the present invention discloses a synergistic effect between administration of flavonoids and the administration of a metal, i.e. a combination therapy with flavonoids and metal is much more efficient than either one alone.

Hence, it is a third objective of the present invention to provide a pharmaceutical composition comprising a pharmaceutical effective amount of a flavonoid and/or a flavonoid derivative and/or a pharmaceutical acceptable salt thereof, as well as a pharmaceutical acceptable metal and/or metal salt and/or metal complex.

It is a further objective of the present invention to provide a kit of parts comprising a pharmaceutical effective amount of a flavonoid and/or a flavonoid derivative and/or a pharmaceutical acceptable salt thereof, as well as a pharmaceutical acceptable metal and/or metal salt and/or metal complex.

It is yet a further objective of the present invention to use a therapeutically effective amount of a flavonoid and/or a flavonoid derivative and/or a pharmaceutical acceptable salt thereof, together with a therapeutically effective amount of a metal and/or metal salt and/or metal complex and a pharmaceutically acceptable carrier for the preparation of a medicament for treatment of one or more conditions and/or symptoms relating to a common cold of the upper and/or lower respiratory tract and/or eyes.

It is another objective of the present invention to provide a method of treatment of an individual, including a human being, comprising administering to said individual either simultaneously as separate or combined formulation or sequentially in any order, a therapeutic effective amount of a flavonoid and/or a flavonoid derivative and/or a pharmaceutical acceptable salt thereof as well as a pharmaceutical acceptable amount of a metal and/or metal salt and/or metal complex for ameliorating, curative and/or prophylactic therapy of one or more conditions and/or symptoms relating to a common cold of the upper and/or lower respiratory tract and/or eyes.

In combination with metal, flavonoid and flavonoid derivatives according to the present invention includes flavonoids of the general formula:

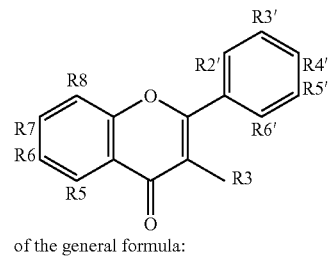

of the general formula:

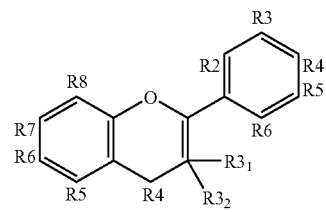

Wherein
R2' can be selected from: —H
—OH
R3' can be selected from: —H
—OH.
—OCH$_3$
—OCH$_2$—CH$_2$OH
R4' can be selected from: —H
—OH
—OCH$_3$
—OCH$_2$CH$_2$OH
R5' can be selected from: —H
—OH
—OCH$_3$
—OCH$_2$CH$_2$OH
R3 including R3$_1$ and R3$_2$ can be selected from:
—H
—OH
—O-rutinose
—O-glucoside
—O-glucose-p-coumaric acid
—SOH
—O-rhamnose
R4 can be selected from: —(O)
—OH
R5 can be selected from: —H
—OH
—O—CH$_2$CH$_2$OH
R6 can be selected from: —H
—OH
—OCH$_3$
R7 can be selected from: —H
—OH
—O-glucose
—OGH$_3$
—OCH$_2$CH$_2$OH
—O-glucuronic acid
—O-rutinose
—O-rhamnoglucoside
R8 can be selected from: —H
—OH.

Furthermore, flavonoid and/or flavonoid derivatives could be stereoisomers of the above mentioned. Additionally flavonoid and/or flavonoid derivatives could be dimers comprising two flavonoid subunits.

Additionally, flavonoids and/or flavonoid derivatives of the present invention to be used in combination with metal could be any flavonoid and/or flavonoid derivative known to the person skilled in the art. For example such flavonoid and/or flavonoid derivative could be any of the flavonoid and/or flavonoid derivative mentioned in WO 01/03681, which is hereby incorporated in its entirety by reference.

Preferably, the flavonoid and/or flavonoid derivatives are selected from molecules with the above general formulas with the proviso,
that when R3' is selected from —OH
—OCH$_3$
—OCH$_2$CH$_2$OH
then R5' is selected from —H
and when R5' is selected from —OH
—OCH$_3$
—OCH$_2$CH$_2$OH
then R3' is selected from —H Semi-synthetic flavonoids are also within the scope of the present invention.

Preferably, the flavonbid according to the present invention could be selected from the group consisting of: troxerutin, venoruton, hydroxyethylrutosides, hesperitin, naringenin, nobiletin, tangeritin, baicalein, galangin, genistein, quercetin, apigenin, kaempferol, fisetin, rutin, luteolin, chrysin, taxifolin, eriodyctol, catecithin, epicatechin, epigallocatechin, epicatechin gallate, epigallocatechin gallate, flavone, sideritoflavone, hypolaetin-8-O-GI, oroxindin, 3-hydroxyflavone, morin, quercetagetin-7-O-GI, tambuiletin, gossypin, hipifolin, naringin, leucocyan idol, amentoflavone and derivatives thereof 'and mixtures' thereof.

More preferably, one or more of the R chains are —OCH$_2$CH$_2$OH, yet more preferably, at least two R chains are —OCH$_2$CH$_2$OH, most preferably three R chains are —OCH$_2$CH$_2$OH.

Preferably, said flavonoid and/or flavonoid derivative does not comprise antiviral activity when tested in vitro. Furthermore, it is, preferred that said flavonoid is soluble in water. More preferably, said flavonoid is a hydroxyethylrutoside, which does not comprise antiviral activity when tested in vitro. Yet more preferably, said flavonoid and/or flavonoid derivative is selected from the group consisting of troxerutin, Veneruton, pharmaceutical acceptable salts thereof and functional derivatives thereof.

In one especially preferred embodiment of the present invention the flavonoid derivative to be used is troxerutin of the formula:

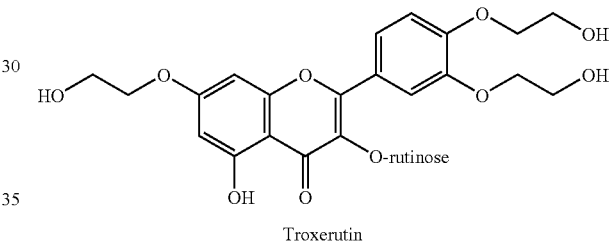

Troxerutin

Mixtures of more than one flavonoid and/or flavonoid derivative is also comprised within the present invention. For example such a mixture may comprise 2, such as 3, for example 4, such as 5, for example 6, such as 7, for example 8, such as 9, for example 10, such as more than 10 different flavonoids. Preferably, such a mixture comprise 8 to 10 different flavonoids.

In one preferred embodiment the flavonoid derivatives according to the invention comprises, a mixture of mono-, di-, tri- and tetrahydroxyethylrutosides. More preferably, the mixture comprise 1% to 15% monohydroxyethylrutoside, such as from 5% to 10% monohydroxyethylrutoside, and from 25% to 50% dihydroxyethylrutoside, such as from 30% to 38% dihydroxyethylrutoside, and, from 30% to 70% trihydroxyethylrutoside, such as from 45% to 55% trihydroxyethylrutoside and from 1% to–20% tetrahydroxyethylrutoside, such as from 3% to 12% tetrahydroxyethylrutoside. Most preferably, said mixture of hydroxyethylrutosides is Venoruton.

FIGURES

Figure 2:
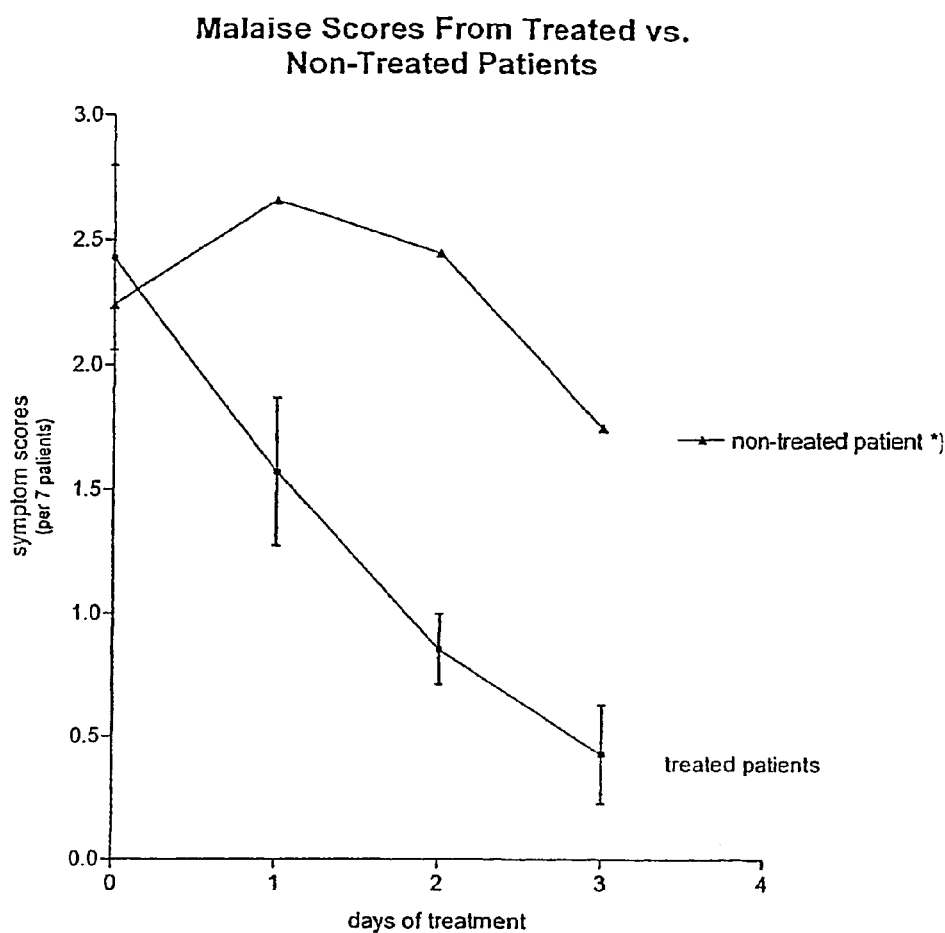

FIG. 1. The number of "events" in each category (symptoms 14) were counted every day. Day 0: no treatment; day 1=24 h treatment, etc. Symptom 4 (very strong), symptom 3 (strong), symptom 2 (not pleasant), symptom 1 (minimal symptoms), symptom 0 (no symptoms):

FIG. 2. The total scores from all patients under the symptom "malaise" were calculated for each day and graphed vs. a so-called "non-treated" group taken from Jackson et al, 1958 (day 2 in Jackon's study is here used as day 0)

Figure 3:
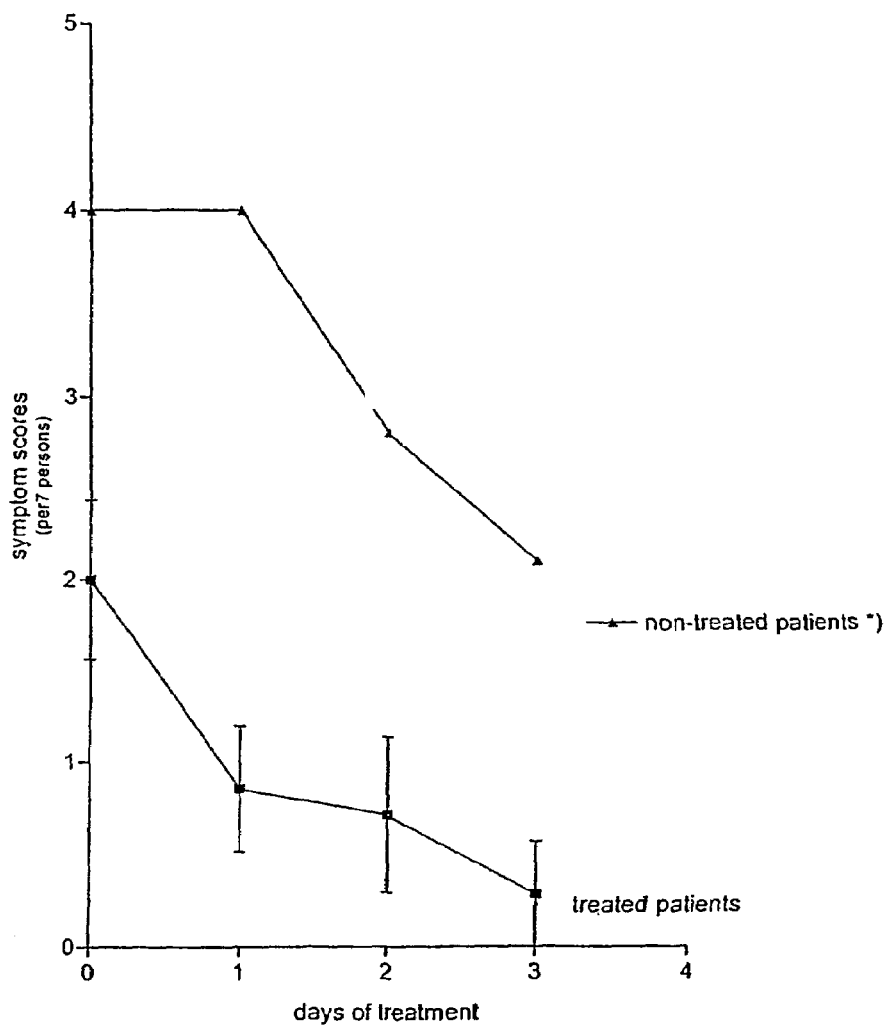

FIG. 3. The scores for the symptom "sore throat" were calculated for each day as in the preceding figure.

Figure 4:
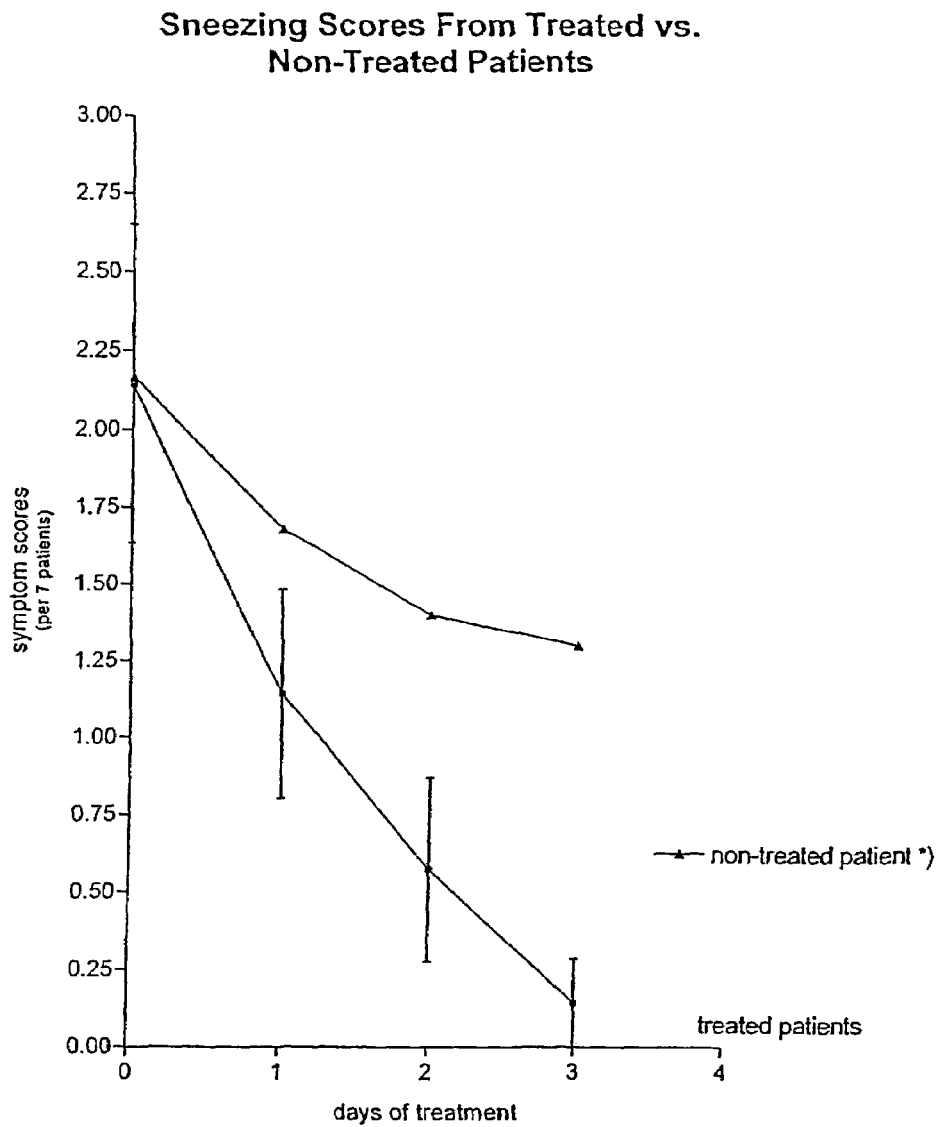

FIG. 4. The corresponding scores for the "sneezing" symptom were calculated as in the preceding figures as an average from 7 patients.

Figure 5:
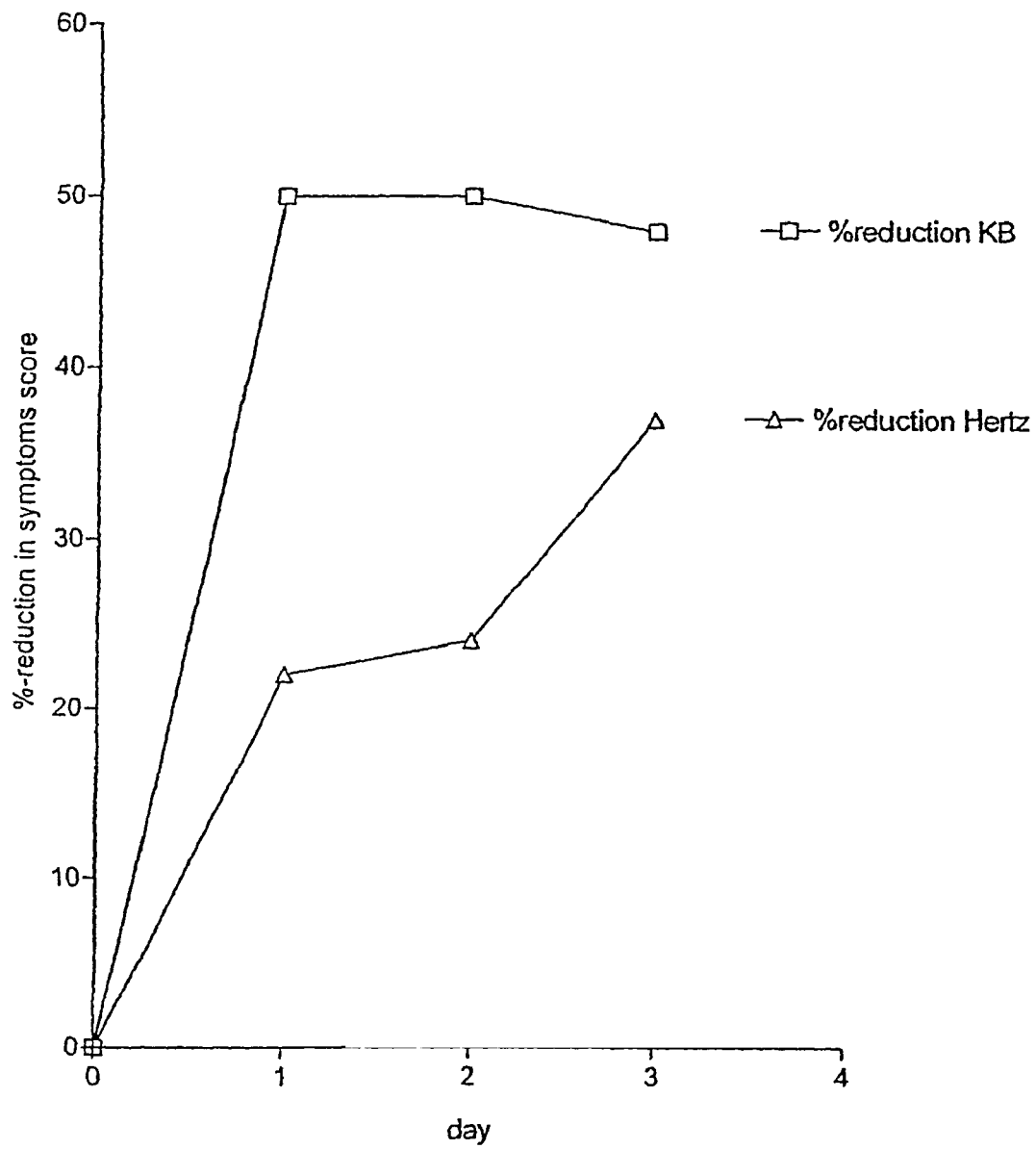

FIG. 5. The mean total scores from a control trial (Hertz) and the trial described in example 1 (KB) are compared as %-reduction in mean total symptom score per patient.

Figure 6:
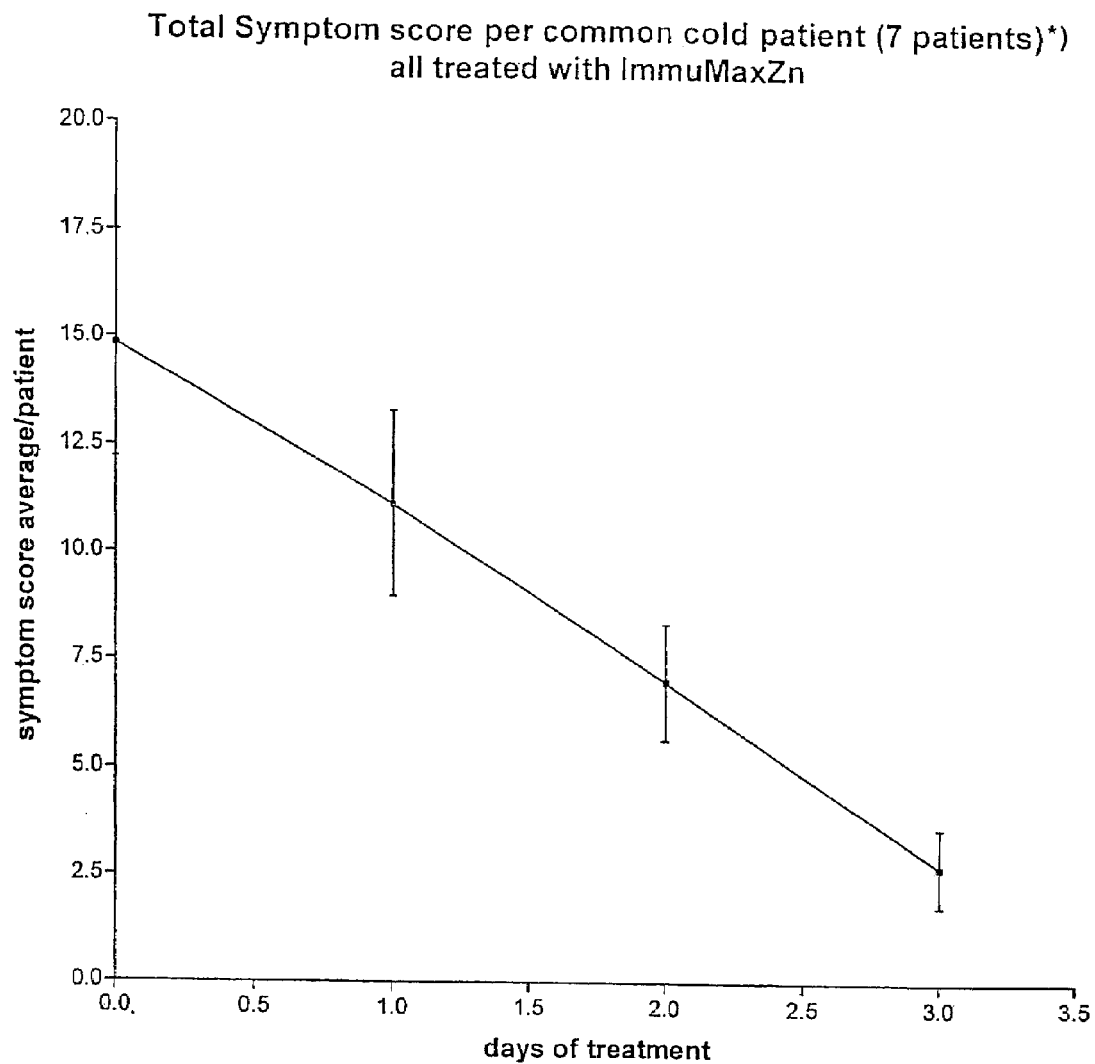

FIG. 6. Average symptom score per patient during a 3 days treatment with preparation C (ImmumaxZn).

Figure 7:
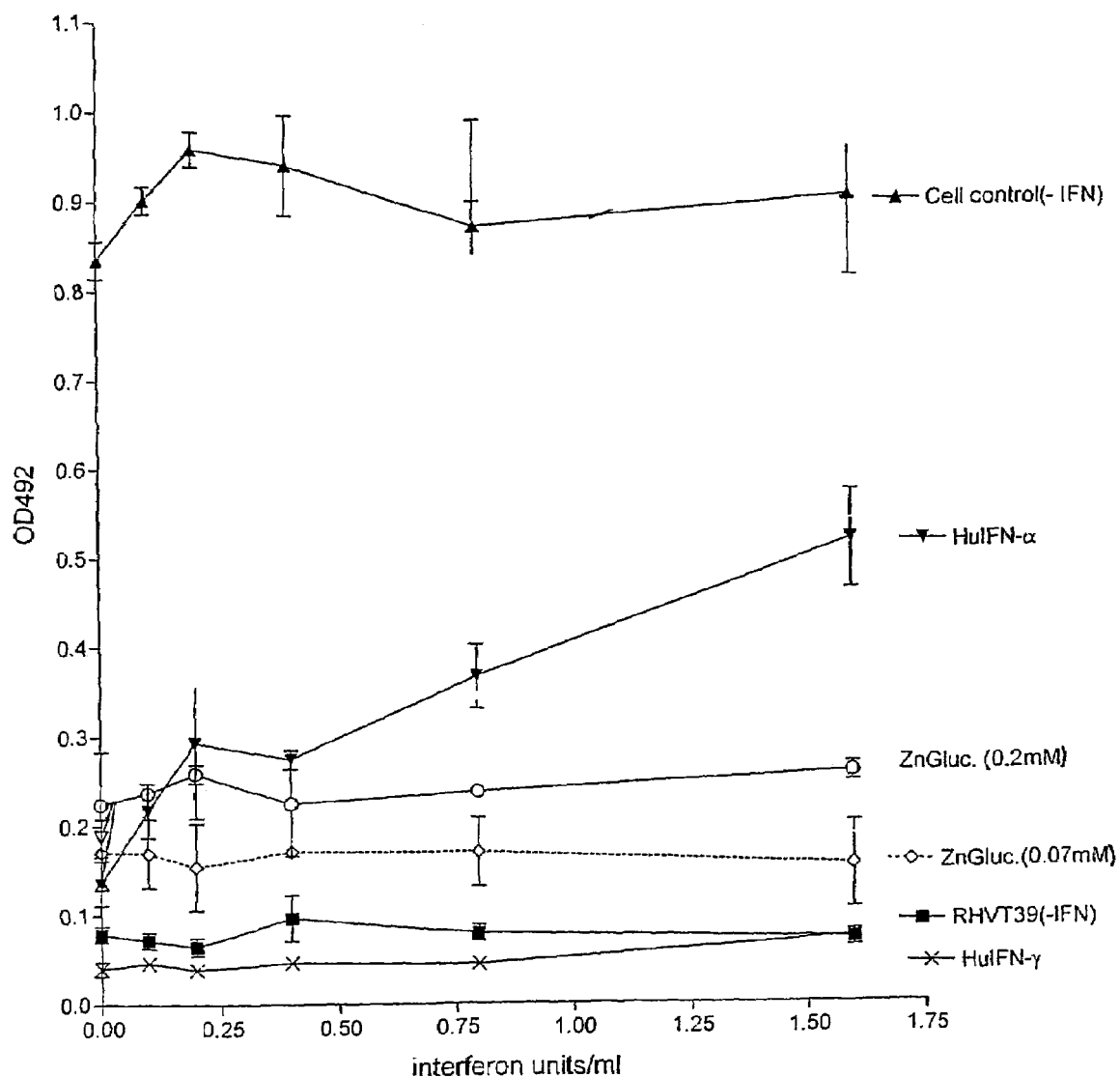

FIG. 7. The antiviral activity of natural HuIFN-α vs. Rhinoviru's-T39

DETAILED DESCRIPTION OF THE INVENTION

According to the present invention conditions relating to a common cold of the upper and/or lower respiratory tract and/or eyes comprises common cold, a viral infection and/or a bacterial infection of the upper and/or lower respiratory tract and/or eyes, rhinitis, an allergic condition having one or more symptoms similar with the symptoms of a common cold for example allergic rhinitis initiated by rhinovirus infection, asthma like exacerbations and/or other abnormal airway functions derived from various dysfunctions of the immune system, such as for example hay fever or the like.

Furthermore, conditions relating to a common cold may comprise secondary bacterial infection(s) that follow soon after a primary viral infection. Secondary bacterial infections may for example be initiated by the normal bacterial flora present in the upper and/or lower respiratory tract and/or eyes.

Symptoms of conditions relating to common cold can be selected from the group comprising, but is not limited to: coughing, sneezing, muscle pain, sore throat, hoarseness, irritated throat, headache, malaise, chilliness, nasal discharge, nasal obstruction, pain relating to the sinuses, fever, rhinitis, swelling of mucosal membranes, pharyngitis, astma, and acute as well as chronic bronchitis.

In the present invention the upper respiratory tract includes the mouth, nose, sinuses, throat, and the respiratory tract to epiglottis. The lower respiratory tract includes the rest of the bronchial tree including the bronchioles and lung vacuoles. The invention also relates to the treatment of eye symptoms related to the condition of the respiratory tract in that the condition may involve the mucosal lining of the respiratory tract as well of the eyes. By the term treatment as used herein is also meant prevention of symptoms whether the prevention is in fact a decrease in the development of symptoms or a prevention of the symptoms to arise in first place, e.g. upon exposure to infection.

According to the present invention a pharmaceutically effective amount or a therapeutically effective amount is to be understood as an amount sufficient to induce a desired biological result. The result can be alleviation of the signs, symptoms, or causes of a disease, for example of common cold, preferably, the result is a significant alleviation of signs, symptoms or causes of common cold. For example, an effective amount is generally that which provides either subjective relief of symptoms or an objectively identifiable improvement as noted by the clinician or other qualified observer, preferably such a relief of symptoms is a significant relief. The relief may for example be evaluated based on a symptom score as disclosed herein in the examples.

Accordingly, effective amounts can vary widely depending on the individual, on the disease or symptom to be treated.

Most common cold patients produce interferon following infection of the respiratory tract (Cate et al., 1969), which per se in principle should be sufficient to alleviate the infection.

Hence, in one preferred aspect of the present invention the treatment of a viral infection is not to be regarded as a direct antiviral effect but as a modification or inhibition of cytokines or other factors relevant for the establishment or continuation of a viral infection located in the mucosal membrane of the respiratory tract or eyes. Furthermore, the treatment preferably inhibits inflammation processes in the mucosal membrane of the respiratory tract or eyes and thereby alleviates symptoms of common cold. Accordingly, the invention relates to use of a flavonoid and/or a flavonoid derivative for the treatment of symptoms of viral infection of the upper and/or lower respiratory tract and/or eyes, wherein the flavonoid and/or flavonoid derivative has no antiviral effect in vitro.

Thus, in one preferred embodiment of the present invention the flavonoid and/or flavonoid derivatives does not comprise an antiviral or anti bacterial effect in vitro. In vitro antiviral and/or antibacterial effect can be determined in various laboratory tests. Preferably, such laboratory tests comprise a cultured cell line capable of being infected with the bacteria or virus to be tested as well as said bacteria or virus. More preferably, said cultured cell line is WISH cells and said virus is a rhinovirus selected from the group consisting of: rhinovirus 1A, rhinovirus 15 and rhinovirus 39. Most preferably antiviral effect is determined using the MTS method as described in example 1. When antiviral effect is measured according to the MTS method as described in example 1, a protection of less than 10%, preferably less than 7.5%, more preferably less than 5%, even more preferably less than 3%, most preferably less than 2% is to be regarded as no antiviral effect in vitro.

Preferably, the effect of the flavonoid and/or flavonoid derivative is closely related to the living organism such as the effect is a modulatory effect on specific factors and biological reactions related to the affected mucosal membrane. The precise mechanisms are currently not known.

Very often common cold is initiated by, associated with or followed by a viral infection which is involved in the common cold or symptoms of the common cold. In one embodiment of the present invention the condition relating to common cold is associated with a viral infection of the upper and/or lower respiratory tract and/or eyes.

The virus infection which a common cold is most often associated with or initiated by, is infection by one or more virus selected from the group consisting of: adenoviruses, parvoviruses, picornaviruses, reoviruses, orthomyxoviruses, paramyxoviruses, arenaviruses, caliciviruses, coronaviruses, orthomyxoviruses, rhinovirus, influenza virus, including influenza virus type A and B, echovirus, respiratory syncytial virus (RSV), and coxsackie virus. Rhinovirus is the most common virus identified in relation to common cold. The term rhinovirus is meant to comprise any rhinovirus for example any of the rhinoviruses 1–113. However, very often the above virus may be present in individuals with no symptoms of common cold. Preferably, the virus infection associated with common cold according to the present invention is infection by rhinovirus or coronavirus.

Very often the common cold is associated with or followed by a bacterial infection, which is involved in the common cold or symptoms of the common cold. Such a bacterial infection may in one embodiment of the, present invention be a secondary infection following a primary infection with for example a virus. In one embodiment of the present invention the condition relating to common cold is associated with a bacterial infection of the upper, and/or lower respiratory tract and/or eyes.

The bacterial infection which may be associated with a common cold or with the symptoms thereof is most often infection by one or more bacteria selected from *Streptococcus pheumoniae, Streptococcus Haemolyticae, Haemophilus influenxae*, and *Moraxella catarrhalis*.

Furthermore, common cold may be initiated by a microbial infection. Such a microbial infection may lead to similar inflammatory responses as viral infections involving the same effector cells for example neutrophiles. Accordingly, such microbial infections may be treated in a fashion similar to viral infections associated with common cold.

Many allergic reactions are associated with symptoms similar to the symptoms of a common cold and it has surprisingly been shown that such symptoms of an allergic disorder may also be effectively treated by the method and use as disclosed herein. Hence, in one embodiment of the present invention the condition relating to common cold is an allergic disorder.

The allergic conditions according to the present invention is preferably selected from rhinitis, asthma, acute and chronic bronchitis, and hay fewer, and the most common symptoms in this respect is one or more symptom selected from nasal discharge, nasal congestion, sneezing, cough, swelling of mucosal membranes, rhinitis. More preferably, the allergic condition according to the present invention is selected from the group consisting of rhinitis and hay fewer. In a further aspect of the present invention the individual may have relief from the symptoms based on a decreasing effect of said flavonoid derivatives on the mucosal swelling associated with the infection or condition mentioned herein. In a still further aspect the present invention encompass acute allergic reactions related to insect bites and sticks and in a still further aspect to the allergic reactions from food or other allergens leading to swelling of the mucosa of the mouth and/or throat in such acute reactions.

It is furthermore contained within the present invention to treat allergic conditions that is initiated by one or more agents selected from the group consisting of: pollution, house dust, common dust mite such as, Dermatophagoides Farinae or Dermatophagoides Pteronyssinus, pollen such as grass pollen, tree pollen or weed pollen, mold, animal danders or feathers, fungal spores and chronic inhalation of for example, wheat flour.

Accordingly, the conditions related to common cold of the present invention could be an infection or common cold or allergic condition characterised by one or more symptoms selected from the group comprising: coughing, sneezing, muscle pain, sore throat, hoarseness, irritated throat, headache, malaise, chilliness, nasal discharge, nasal obstruction, pain relating to the sinuses, rhinitis, swelling of mucosal membranes, pharyngitis, astma, and acute as well as chronic bronchitis.

When the condition relating to common cold is an allergic condition, preferably such a condition is treated by administration of flavonoid without simultaneous administration of metal to the individual in need thereof. More preferably said flavonoid is selected from the group consisting of troxerutin and Veneruton®.

The classical common cold results in symptoms, which lasts for approximately one week. However, in certain cases conditions relating to common cold results in symptoms, which lasts for much longer. Such long lasting common colds for example last for more than 10 days, such as more than 2 weeks, such as more than 3 weeks, for example more than one month, such as more than 6 weeks. Individual suffering from long lasting common cold are preferably treated by administration of flavonoid without simultaneous administration of metal. More preferably said flavonoid is selected from the group consisting of troxerutin and Veneruton®.

In contrast, individuals suffering from a classical common cold wherein treatment is initiated 1 to 5 days following the onset of common cold symptoms, preferably 1 to 3 days following the onset of common cold symptoms are preferably treated by administration of both a flavonoid and metal according to the present invention.

In one preferred embodiment the flavonoid and/or flavonoid derivative is not able to potentiate interferon mediated antiviral activity. Preferably, determination of potentiation of interferon mediated antiviral activity is performed using a laboratory test measuring antiviral effect as described herein above; Such, laboratory test preferably includes measuring the antiviral effect of interferon in the presence and absence of said flavonoid and/or derivatives. More preferably such test is performed as described in example 3 and 4.

The interferons could be any interferon known to the person skilled in the art. Such interferon could be derived from a mammal including a human being. Such interferon could be naturally occuring interferon and/or recombinant interferon. Preferably such interferon could be selected from the group consisting of: IFN-$\alpha$, IFN-$\beta$, IFN-$\gamma$ and native human leucocyte interferon. More preferably, such interferon could be HuLFN-$\alpha$-2b.

The effective dosage of said flavonoids and/or flavonoids derivatives and/or a pharmaceutically acceptable salt thereof is preferably from 5 to 5000 mg daily. More preferably, the effective dosage is from 10 mg to 4000 mg, such as from 30 mg to 3000 mg, even more preferably from 40 mg to 2000 mg daily, yet more preferably, from 50 mg to 1000 mg daily.

Furthermore, the effective dosage of said flavonoids and/or flavonoids derivatives and/or a pharmaceutically acceptable salt thereof could be a dosage equivalent of a dosage of troxerutin of from 5 mg to, 5000 mg daily.

The effective dosage of Venoruton or troxerutin or a pharmaceutically acceptable salt or a functional derivative thereof is from 5 to 5000 mg. In general the effective dosage is from 10 mg to 4000 mg, such as from 30 mg to 3000 mg, preferably from 40 mg to 2000 mg daily, more preferably, from 50 mg to 1000 mg daily, yet more preferably from 50 to 500 mg daily, most preferably from 100 to 300 mg daily.

The administration of flavonoids and/or flavonoid derivatives according to the present invention is preferably a very frequent administration during the day. Accordingly, the daily dosage may be administered in divided dosages of 1 to 36 individual dosages daily, preferably 2 to 24 times daily, more preferably 3 to 12 times daily, such as 5 to 8 times daily, for example around 6 times daily. Preferably, the first 2 doses are administrated simultaneously. The specific number of daily applications may be correlated to the individual way of administration and the severity of the symptom in question. The preferred treatment is a treatment where the medicament is present in the mucosal membrane as constant as possible due to the theory that the individual factors involved in the maintenance of the symptoms are constantly produced in the affected mucosal membrane during the illness.

In one embodiment the flavonoids or the composition or kit-of-parts comprising flavonoids and metals according to the present invention are administered in combination with a second treatment such as in combination with an antiviral treatment including treatment against influenza such as TaMiFlu®, treatment against rhinitis such as' Picovir®; or treatment with antibodies against streptococcus; or treatment with interferons (alpha, beta or gamma) and mixtures thereof. The antiviral agents include TamiFlu or other neuraminidase inhibitors or rimantadine or antibodies against RSV.

In another embodiment of the present invention the second treatment is administration of an anti-microbial agent. Preferably, the anti-microbial agent is distinct and specific, however the anti-microbial agent may also be a general antibiotic. In particular, an anti-microbial agent may be administrated to treat conditions associated with bacterial infections.

However, the flavonoids according to the present invention may be administered alone or in combination with a metal (see below). In particular, the flavonoids according to the present invention are preferably not administrated in combination with a vitamin.

In one preferred embodiment the flavonoids are comprised in a composition or a kit of parts that further comprises a therapeutic effective amount of a metal and/or metal salt and/or complex or derivatives thereof.

The metal according to the present invention is preferably selected from the group consisting of zinc, manganese, cadmium, cobalt, iron and selenium. The metal may for example be in the form of $Zn^{2+}$, $Mn^{2+}$, $Cd^{2+}$, $Co^{2+}$, $Fe^{2+}$ and $Se^{2+}$. Most preferably the metal is zinc. Preferably zinc is $Zn^{2+}$, given in the form of a salt and/or complex or derivatives thereof.

Within the scope of the present invention, zinc could be in any suitable form for example as ZnGluconate, as Zn(acetate)$_2$, as $Zn^{2+}$ aminochelates, as $Zn^{2+}$ amino acid chelates, as $Zn^{2+}$ DL-methionine, as $Zn^{2+}$ L-methionine, as histidine derivatives or as a complex with amino acids in combination with histidine, or the like such as for example PolaPreZinc®. Furthermore zinc could be in the form of zinc sulfate, zinc chloride, Nitric-acid zinc, phosphoric-acid zinc, ulmin acid zinc, zinc fluoride, zinc iodide, a zinc hydroxide, zinc carbonate, a zinc chromate, benzoic-acid zinc, zinc acetate, p-aminobenzoic-acid zinc, p-dimethylamino benzoic-acid zinc, p-zinc phenolsulfonate, p-methoxy cinnamic-acid zinc, lactic-acid zinc, gluconic-acid zinc, citric-acid zinc, salicylic-acid zinc, a zinc stearate, lauric-acid zinc, myristic-acid zinc, Oleic-acid zinc, 2,5-pyridine dicarboxylic-acid zinc, 2, 6-pyridine dicarboxylic-acid zinc, 4-pyridine dicarboxylic-acid zinc, 2,4-dicarboxy pyridine zinc, 3-hydroxy-2-carboxy pyridine zinc, 3-n-propoxy-2-carboxy pyridine zinc, 3-n-hexyloxy-2-carboxy pyridine zinc, 5-n-propoxy-2-carboxy pyridine zinc, 5-n-butoxy-2-carboxy pyridine zinc, 5-(2-ethyl-hexyloxy-2-carboxy pyridine zinc, 6-n-butoxy-2-carboxy pyridine zinc, 3-methoxy-2-carboxy pyridine zinc, 5-methoxy-2-carboxy pyridine zinc, 6-methoxy-2-carboxy pyridine zinc, 6-n-hexyloxy-2-carboxy pyridine zinc, 3-methyl-2-carboxy pyridine zinc, 4-methyl-2-carboxy pyridine zinc, 4-tert-butyl-2-carboxy pyridine zinc, 5-methyl-2-carboxy pyridine zinc, 5-n-hexyl-2-carboxy pyridine zinc, 3-n-undecyl-2-carboxy pyridine zinc, 4-n-undecyl-2-carboxy pyridine zinc, 5-n-butyl-2-carboxy pyridine zinc, 6-n-undecyl-2-carboxy pyridine zinc, 4-nitroglycerine-2-carboxy pyridine zinc, 5-hydroxy-2-carboxy pyridine zinc, 4-fluoro-2-carboxy pyridine zinc, 2-carboxy pyridine N-oxide zinc, picolinic-acid zinc, Nicotinic-acid zinc, nicotinamide zinc, 3,4-dihydroxy benzoic-acid zinc, Screw histidine zinc, hinokitiol zinc, protoporphyrin zinc, porphyrin zinc or picolinic-acid amide zinc.

It is contained within the present invention that zinc could be a combination of the above mentioned zinc salts and/or a zinc complexes. Such combination could comprise two or more sorts. Preferably zinc is selected from the group consisting of $Zn^{2+}$ aminochelates, $Zn^{2+}$ amino acid chelates, Zn(acetate)$_2$, $Zn^{2+}$ DL-methionine, $Zn^{2+}$ L-methionine, ZnGluconate and PolaPreZinc®. Preferably, zinc is in the form of ZnGluconate or PolaPreZinc (.

The effective dosage of Zinc depends' upon the form of zinc component which is adminstrated. Preferably between 0.1 mg and 500 mg $Zn^{2+}$ is administrated, such as between 0.5 mg and 250 mg, for example between 1 mg and 150 mg, such as between 5 mg and 100 mg, for example between 10 mg and 50 mg per dose. If the zinc compound is ZnGluconate, preferably between 5 mg and 1000 mg, rmore preferably between 10 mg and 500 mg, even more preferably between 10 mg and 100 mg, yet more preferably between 20 mg and 80 mg, even more preferably between 30 mg and 70 mg, most preferably around 50 mg ZnGluconate is administrated per dose. If the zinc compound is PolaPreZinc, preferably between 1 mg and 500 mg, more preferably between 5 mg and 250 mg, even more preferably between 10 mg and 100 mg, most preferably around 25 mg.

The administration of a flavonoid and/or a flavonoid derivative and/or a pharmaceutical acceptable salt thereof and a pharmaceutical acceptable amount of a metal and/or metal salt and/or metal complex may be either simultaneously as separate or combined formulations or it may be sequential.

It is preferred to present flavonoids and/or flavonoid derivatives and/or metals according to the present invention in the form of a pharmaceutical formulation. Accordingly, the present invention further provides pharmaceutical formulations, either as a single composition or as a kit of parts, for medicinal application, which comprises a flavonoid and/or flavonoid derivative as well as a metal and/or metal salt and/or metal complex according to the present invention or a pharmaceutically acceptable salts thereof, as herein defined, and a pharmaceutically acceptable carrier therefore.

The pharmaceutical formulations according to the present invention may be prepared by conventional techniques, e.g. as described in Remington: The Science and Practice of Pharmacy 1995, edited by E. W. Martin, Mack Publishing Company, 19th edition, Easton, Pa. The pharmaceutical formulation may have any form known to the person skilled in the art. For example the pharmaceutical formulation may be in the form of a solution, dispersion, emulsion, suspension, bioadhesive and non-bioadhesive gel, powder, micropheres, tablets, lozenges, chewing tablets, chewing gum, pills, capsules, cachets, suppositories, dispersible granules, drops, sprays, aerosols, insufflators, inhalators, patches, a lollipop, ointment, lotion, cream, foam, implant, syrup or balm. The skilled person may select the appropriate administration form based on the common knowledge within the field of delivery systems for pharmaceuticals.

It is believed that the optimal effect is obtained by a direct topical application of the flavonoids and/or metals according to the present invention on the mucosal membrane in question. Accordingly, it is preferred that the administration is topical administration directly to the mucosal membrane, more preferably, to the mucosal membrane of the upper and/or lower respiratory tract and/or of the eyes, even more preferably the mucosal membrane of the oral cavity. The formulation should generally be distributed to a major part of the mucosal involved in the specific condition or symptom to be treated.

The pharmaceutical composition and/or the kit of parts according to the present invention usually comprise pharmaceutically acceptable carriers, which can be either solid or liquid. Carrier can be one or more substances which may also act as diluents, flavouring agents, solubilisers, lubricants, suspending agents, binders, preservatives, wetting agents, tablet disintegrating agents, or an encapsulating material. Such carriers include pharmaceutical grades of mannitol, lactose, starch, magnesium stearate, sodium saccharine, talcum, cellulose, glucose, lactose, pectin, dextrin, starch, gelatin, sucrose, magnesium carbonate, tragacanth, methylcellulose, sodium carboxymethylcellulose, a low melting wax, cocoa butter, and the like. Preferably, the pharmaceutical carrier is Magnesium stearate. In addition, the pharmaceutical formulations may comprise colorants, flavours, stabilisers, buffers, artificial and natural sweeteners, dispersants, thickeners, solubilising agents, and the like.

In powders, the carrier is a finely divided solid, which is a mixture with the finely divided active components. In tablets, the active components are mixed with the carrier having the necessary binding capacity in suitable proportions and compacted in the shape and size desired. The powders and tablets preferably contains from one to about seventy percent of the active compound.

Formulations suitable for topical administration in the mouth include lozenges comprising active agents in a flavoured base, usually sucrose and acacia or tragacanth; pastlles' comprising the active ingredient in an inert base such as gelatin and glycerin or sucrose and acacia; and mouthwashes comprising the active ingredient in a suitable liquid carrier. In one preferred embodiment the lozenges comprise sorbitol and/or peppermint oil.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Surprisingly, the present invention discloses that even though common cold is usually caused by an infection of the upper and/or lower respiratory tract, it can be treated effectively by topical administration directly to the mucosal membrane of the oral cavity. Since administration directly to the mucosal membrane of the oral cavity is very convenient for the individual to be treated, it is a considerable advantage of the present invention that administration can be performed directly to said mucosal membrane. In addition, the present invention discloses that allergic rhinitis also can be treated by applying the compounds according to the present invention directly to the musocal membrane of the oral cavity. Accordingly, the compounds according to the present invention are preferably formulated as lozenges, chewing tablets, chewing gum, drops, sprays and aerosols, which can be applied directly to the mucosal membrane of the oral cavity. Most preferably, the compounds according to the present invention are formulated as lozenges, which can be directly applied to the mucosal membrane of the oral cavity.

The individual in need of a treatment according to the invention could be any individual, however preferably, such individual is a human being. The individual will generally have a score relating to symptoms based on the score system as disclosed in Patients diary, (see examples) of at least 4 to 5, such as at least 6 preferably, at least 10, more preferably the patient would have a score of at least 15, whereas an individual with a score of 3 or less is not to be regarded as sick. Generally speaking a score around 5 to 6 or lower will allow the person to continue his/her work.

In a further aspect of the invention, the treatment results in a decrease in the severity of symptoms corresponding to a decrease of score as measured according to patients diary herein of at least 15% within 24 hours, such as least 25%, more preferably of at least 30% in 24 hours from the start of the treatment. After 48 hours of treatment the scores is preferably decreased with at least 20% in 48 hours, such as with at least 30%, for example with around 40% to 60%, more preferably with at least 40%, yet more preferably with at least 50%, even more preferably with at least 60% in 48 hours from the start of the treatment. 72 hours of treatment preferably results in a decrease of score as measured according to Patients Diary herein of at least 30%, preferably at least 40%, more preferably at least 50%, even more preferably at least 55%, yet more preferably at least 59%, even more preferably at least 65%, most preferably at least 70% in 72 hours from the start of the treatment. However, the preferred decrease in symptom score is dependent on the condition relating to common cold to be treated, the scheme of treatment and the individual patient.

Flavonoids are known to possess anti-oxidative properties, and according to one further aspect, the flavonoid is a flavonoid having a singlet Oxygen Quenching measured 'as the rate constant of '02 quenching K of from $10^4$ to $10^9$ $M^{-1}$ $s^{-1}$. Preferably, the rate is $10^4$ to $10^8$ $M^{-1}$ $s^{-1}$. The singlet oxygen quenching can be measured using a variety of solvents known to the person skilled in the art. Preferably, the solvent is selected from the group consisting of $CD_3OD$, a mixture of $CCl_4$ and $CH_3OH$ of 1:3 and $CH_3CN$.

EXAMPLES

| Preparation A (Immumax) | |
|---|---|
| Venoruton ® | 50 mg |
| Sorbitol | 934 mg |
| Peppermint oil | 8 mg |
| Magnesiumstearat | 10 mg |
| In total | 1000 mg |

| Preparation B | |
|---|---|
| Troxerutin | 50 mg |
| Sorbitol | 934 mg |
| Peppermint oil | 8 mg |
| Magnesiumstearat | 10 mg |
| In total | 1000 mg |

| Preparation C (ImmuMaxZn) | |
|---|---|
| Venoruton ® (Novartis) | 50 mg |
| Zn Gluconate (Fertin) | 50 mg |
| Sorbitol | 882 mg |
| Peppermint oil | 8 mg |
| Magnesiumstearat | 10 mg |
| In total | 1000 mg |

Patients diary

This scheme should preferably be filled out in the evening. How are your current condition with regard to the symptoms below. In the scheme below, please state the strength of your symptoms today by inserting an X at the appropriate place: every symptom should have points: 0 means that you have not had any symptoms at all; 4 means that you have had the worst symptoms available; etc. 0 = no symptoms, 1 = a minimum of symptoms; 2 = unpleasant symptoms; 3 = considerably unpleasant symptoms; 4 = very unpleasant symptoms

| | Symptom points | | | | |
|---|---|---|---|---|---|
| | 0 | 1 | 2 | 3 | 4 |
| Cough | | | | | |
| Headache | | | | | |
| Hoarseness | | | | | |
| Nasal discharge | | | | | |
| Sneezing | | | | | |
| Nasal obstruction | | | | | |
| Sore throat | | | | | |
| Irritated throat | | | | | |
| Malaise | | | | | |
| Sore muscles | | | | | |
| Fever | | | | | |

Have you had any side effects of the treatment? Yes ☐ No ☐
Specify _____
Do you also take any other medical treatment or other kinds of treatment apart from this test treatment ? Yes ☐ No ☐
Specify _____

The scheme above may preferable be used for identifying persons in need of a treatment according to the invention and to compare the effect with other treatments or placebo. A total score of 3 to 5 or less is regarded to be a normal condition.

Example 1

Virus Titrations

Rhinovirus 1A, rhinovirus 15 and rhinovirus 39 were titrated according to the tetra zolium salt (MTS)-method (Berg et al., 1989; Berg and Owen, 2001a, Hansen et al., 1989). WISH cells were seeded in a micro tray at 3000 cells per well and incubated at 37° C., 5% $CO_2$ overnight; the following morning the medium was replaced with 10-fold dilutions of either rhinovirus 1A, rhinovirus 15 or rhinovirus 39, respectively, in fresh medium and the trays were incubated 4–5 days at 33° C.; a microscopical examination confirmed that the CytoPathogenic Effect (CPE) was fully developed (CPE equal to 100%). The minimal amount of virus (i.e.: the highest dilution of the virus in question) which produced 100% destruction was used as "challenge virus" in the subsequent experiments. To'quantitate the CPE in terms of % destruction, MTS (Berg and Owen, 2001 a) was added to all 25 cultures and after 3 h incubation at 37° C. (without $CO_2$) the trays were read in a scanner as previuosly described (Berg et al, 1989, Hansen et al., 1989). Control cell cultures, that were not infected with virus, were included in the experiment; the latter gave the highest OD as these cells were not damaged; depending on the concentration of virus added to the different wells, the $OD_{492}$ varied, accordingly: 100% CPE yielded a low OD(<0.200); 0% CPE corresponding to no infection at all (controls cell) gave a high OD (>1.200).

Example 2

No Antiviral Activity of ZnGluconate as Measured Via the MTS-System

WISH cells were seeded in wells in a microtray and incubated for 24 h at 34° C., 5% $CO_2$; the medium was replaced with fresh medium comprising 2-fold dilutions of ZnGluconate (diluted 1:10 from a 1% stock dilutions) and incubated further for 34 days at 33° C., 5% $CO_2$; on the following day challenge virus was added and after 3–5 days at 33° C., 5% $CO_2$, MTS was added and the microtray was measured in an OD-scanner (Berg et al., 1989; Hansen et al., 1989). Alternatively, instead of ZnGluconate WISH cells were incubated with other zinc salts/complexes or with the flavondid derivatives, Troxerutin, Veneruton® or Quercetin.

No substantial protection against rhinovirus by addition of ZnGluconate could be detected (<2% protection). The OD signals from the wells, that were incubated in the presence of ZnGluconate were very close to the virus control curves (FIG. 7). Similar results were observed when testing the antiviral effect of other zinc salts/complexes. When the flavonoid derivatives, Troxerutin and Veneruton were added to the WISH cells, they also did not show any antiviral activity (<1% protection). However Quercetin, had a moderate antiviral activity at levels not toxic to the cells (10 to 15% protection).

Example 3

Antiviral Activity of Interferon-α (rHuIFN-α-2b) Against Rhino Virus (1A, 15 or 39)

3.000 WISH cells were seeded in a microtray and on the following morning, the medium was replaced with 2-fold dilutions (from a 0–30 units/ml stock solution) of HufFN-α-2b (Intron A) in fresh medium comprising 2% serum. After incubation overnight, the medium was replaced with fresh medium comprising challenge virus and incubated at 33° C., 5% $CO_2$ for 3–5 days and processed further as described in Example 2.

The results in FIG. 7 clearly demonstrates that rhinoviruses are reasonable sensitive to HuIFN-α-2b (50% protection). However, 90–100% protection can be achieved at approx. 8–15 units/ml.

Example 4

Troxerutin and Interferon-α (rHuIFN-α-2b) Vs. Rhino Virus (1A, 15 or 39)

An experiment similar to Example 3 was carried out in which various, but constant concentrations of either Troxerutin or Veneruton or other relevant derivatives were added together with the 2-fold dilutions of interferon to WISH cells. A typical example from this series of experiments yielded no potentiation of the interferon system, (<1%) at all at Troxerutin levels below 2.5 mg/ml. Troxerutin concentrations higher than 2.5 mg/ml are toxic to the cells.

Example 5

Rhinitis and Common Cold

Preliminary Trial Involving 2 Persons

Case 1

A) A 60 year old healthy man acquired a rhinitis with occasionally coughs. The person applied one tablet (preparation B) under his tongue and allowed the tablet to melt slowly during a period of 4–5 min. after the period of which the rhinitis sensation gradually disappeared within 10 min. (no more rhinitis, no more coughing).

The rhinitis started again after approx. 20–30 min. and the person applied 1–2 more tablets. (preparation B) as described above after which no more rhinitis was observed. A mild headache disappeared. No side effects were noticed. The rapid effect of the treatment strongly suggests that the effect is caused by local action of the pharmaceutical rather than by systemic action.

The same person had previously on a few occasions treated himself with 1–2 lozenges (preparation B) when a mild rhinitis appeared and each time one lozenge stopped the rhinitis.

Case 2

B) A 57 year healthy woman began coughing and an early rhinitis as described above appeared; the person applied one tablet (preparation B) under her tongue and kept it for 0.3–5 min. When asked about the result a few hours later she reported that the rhinitis had disappeared during 3045 min. after one tablet, only. No side effects were noticed.

Preliminary Conclusion on Case 1 and 2

It appears that the oral treatments comprising 1–3 preparation B tablets have been efficient as the early rhinitis and coughing disappeared. The persons did not catch new rhinitis or colds during the following 4–8 weeks period (ending Dec. 15, 1999).

C) Preliminary Trial Involving 7 Common Cold Patients at Doctor's Office

Based on the above results it was decided to go into a small controlled trial involving 10–15 patients who had acquired the infection naturally and were treated subsequently at a doctor's Office (HA). The optimal season for the classical common cold is from September to February but unfortunately it was not possible to arrange for a small controlled "trial" before the end of March, 2000.

Patient Treatment

Patients reporting to Doctor's Office (HA) complaining of a cold with rhinitis or a strong pharyngitis or other common cold syndromes (cf. Patient's Diary) were asked to fill out the Patients Diary (see above) which included relevant medical examinations (age, sex, patients on medical treatment were excluded, the date for the onset of the cold symptoms as listed in the diary—cf. enclosed copy. No specific efforts other than the usual symptoms of common cold were employed for characterisation of the patients enrolled. Thus most of the patients had experienced the cold for at least 1–2 days before reporting to the Doctor's Office. It is fair to assume that the patients probably represent a group of patient with a more severe cold than Others not reporting to the Office.

A total of 7 patients with the usual characteristics for common cold—cf. the enclosed copy of the Patient's Diary above—were treated with the ImmuMax lozenges (preparation A) described above (50 mg Venoruton®) for a total period of 3 days, only. Each patient was instructed to fill out the patients diary every day (day $0=1^{st}$ visit to the Doctor's Office) and to follow the mode of administration: one lozenge should be applied on or under the patient's tongue and it should melt in a minimum period of 4–5 min. (no fluid or food should be taken the next 15–20 min.) If necessary, the patient could take the next lozenge after 30 min.; a total number of 5 lozenges per day was equal to the maximal dose per day.

The patients were asked to fill out the diaries and to return them to Doctor's Office a few days after the treatment.

Results

The results of this very limited and preliminary trial are shown in tables 1–8 and summarised in FIGS. 1–6. Events are defined as the number of marks noted in the 5 different symptoms categories. The data in table 1/FIG. 1, which shows the number of events per day from the 7 patients in 5 symptom categories, supports the "early" preliminary "trial" as most of the severe symptoms have disappeared after 48 h; after further 24 h the patients have recovered almost completely. The curve for symptom 4 (very strong) drops within the first 24 h and stays at almost 0 for the remainder 48 h. The curve for symptom 3 (strong) had 15 counts on day 0; the curve drops in parallel to symptom 4 curve and at day 2(=48 h treatment) no more counts with symptom 3 are reported from the 0.7 patients. The curve for symptom 2 drops in parallel with the two preceding curves, at day 3, three counts for symptom 2 were reported. The curve for symptom 1 reaches a plateau on day 1 and drops at day 3 to 8 counts. The symptom 0 curve shows 8 counts at day 1; then it rises in parallel to symptom curve 3 during the first 24 h, but it continues to rise to 45 on day 3.

In conclusion it can be stated that the fact that the symptom event score curve rises to a maximum for symptom zero supports the earlier findings with the two persons who were also cured within two days time:

As each patient fills out the diary each symptom receives a score graded from 0–4. These scores were compared with a "non-treated" control group taken from Jackson et al, Arch. Internal. Med. 101:267–278, 1958 (day 2 in Jackon's study is here used as day 0); The total scores from all patients under the syndrome "malaise" were compared with the so-called "non-treated" group The treated patients curve drops almost as a straight line in contrast to the non-treated, but infectious patients curve. At day 3 the treated group has significantly less scores compared to the non-treated group (FIG. 2, table 2 and 3). Similarly the scores for sore throat are significantly reduced after 3 days treatment compared to the non-treated group (FIG. 3, table 4 and 5). The scores for sneezing are close to zero after 3 days of treatment in contrast to the non-treated group (FIG. 4, table 6 and 7).

Furthermore this study were compared with a controlled trial, designated Hertz, with 23 common cold patients who received a spray with another test drug for 6 days the outcome was judged as negative although some minor effects were seen. This trial served as a control group for non-treated patients (placebo). When the mean total scores from these two groups are compared as percent reduction the present trial yielded a 50% reduction in symptom scores each day compared to the Hertz trial showing varying reductions. Based on this comparison it can be argued that the present trial yields a significant reduction in symptom scores compared to the placebo study.

TABLE 1

| x values day | A symptom 0 Y | B symptom 1 Y | C symptom 2 Y | D symptom 3 Y | E symptom 4 Y | sum |
|---|---|---|---|---|---|---|
| 1 | 0 | 8 | 6 | 20 | 15 | 6 | 55 |
| 2 | 1 | 9 | 22 | 15 | 8 | 0 | 54 |
| 3 | 2 | 26 | 23 | 5 | 0 | 1 | 55 |
| 4 | 3 | 45 | 7 | 3 | 0 | 0 | 55 |

The number of events in each category (symptom 1–4) were counted every day, symptom 4 (very strong), symptom 3 (strong), symptom 2 (not pleasant), symptom 1 (minimal symptoms), symptom 0 (no symptom

TABLE 2

| | A treated patients | | | | | | |
|---|---|---|---|---|---|---|---|
| X values day X | Y1 | Y2 | Y3 | Y4 | Y5 | Y6 | Y7 |
| 1 | 0 | 2 | 3 | 3 | 2 | 1 | 4 | 2 |
| 2 | 1 | 2 | 2 | 1 | 1 | 1 | 3 | 1 |
| 3 | 2 | 1 | 1 | 1 | 0 | 1 | 1 | 1 |
| 4 | 3 | 1 | 0 | 0 | 0 | 0 | 1 | 1 |

Malaise scores from patient Y1–Y7 from day 0–3

TABLE 3

| | B non-treated patients | | | | | | |
|---|---|---|---|---|---|---|---|
| | Y1 | Y2 | Y3 | Y4 | Y5 | Y6 | Y7 |
| 1 | 2.240 | | | | | | |
| 2 | 2.660 | | | | | | |
| 3 | 2.450 | | | | | | |
| 4 | 1.750 | | | | | | |

Malaise scores from control group

TABLE 4

| | A treated patients | | | | | | |
|---|---|---|---|---|---|---|---|
| X values day X | Y1 | Y2 | Y3 | Y4 | Y5 | Y6 | Y7 |
| 1 | 0 | 0 | 2 | 2 | 3 | 3 | 1 | 3 |
| 2 | 1 | 0 | 2 | 1 | 1 | 0 | 0 | 2 |

TABLE 4-continued

| | A treated patients | | | | | | |
|---|---|---|---|---|---|---|---|
| X values day X | Y1 | Y2 | Y3 | Y4 | Y5 | Y6 | Y7 |
| 3 | 2 | 0 | 1 | 1 | 0 | 0 | 0 | 3 |
| 4 | 3 | 0 | 0 | 0 | 0 | 0 | 0 | 2 |

Sore throat scores from patient Y1–Y7 from day 0–3

TABLE 5

| | B non-treated patients | | | | | | |
|---|---|---|---|---|---|---|---|
| | Y1 | Y2 | Y3 | Y4 | Y5 | Y6 | Y7 |
| 1 | 4.0 | | | | | | |
| 2 | 4.0 | | | | | | |
| 3 | 2.8 | | | | | | |
| 4 | 2.1 | | | | | | |

Sore throat scores from untreated group

TABLE 6

| | A treated patients | | | | | | |
|---|---|---|---|---|---|---|---|
| X values day X | Y1 | Y2 | Y3 | Y4 | Y5 | Y6 | Y7 |
| 1 | 0 | 1 | 3 | 2 | 3 | 4 | 0 | 2 |
| 2 | 1 | 0 | 2 | 1 | 1 | 2 | 0 | 2 |
| 3 | 2 | 0 | 1 | 1 | 0 | 0 | 0 | 2 |
| 4 | 3 | 0 | 0 | 0 | 0 | 0 | 0 | 1 |

Sneezing scores from patient Y1–Y7 from day 0–3

TABLE 7

| | B non-treated patients | | | | | | |
|---|---|---|---|---|---|---|---|
| | Y1 | Y2 | Y3 | Y4 | Y5 | Y6 | Y7 |
| 1 | 2.170 | | | | | | |
| 2 | 1.680 | | | | | | |
| 3 | 1.400 | | | | | | |
| 4 | 1.300 | | | | | | |

Sneezing scores from control group

TABLE 8

| X values day X | A % reduction K Y | B reduction HE Y | C Data Set-C Y | D Data Set-D Y | E Data Set-E Y |
|---|---|---|---|---|---|
| 1 | 0 | 0 | 0 | | |
| 2 | 1 | 50 | 22 | | |
| 3 | 2 | 50 | 24 | | |
| 4 | 3 | 48 | 37 | | |

Percent reduction in total symptom score. K is this trial, HE is the Hertz trial Conclusions from the Preliminary Trial with 7 Patients Based on the findings in FIGS. 1–5 it appears that the common cold patients are cured significantly faster than the non-treated group as the common cold period is cut down with approx. 50% from 6–7 days to 2–3 days. Furthermore, the more annoying symptoms seem to be cleared already during the first 24 h.

Example 6

Preliminary Trial with 3 Patients Suffering from Allergic Airway Conditions

Case 1

A 56-year old patient (BK/230244) who was allergic to grass and birch pollen was seeking advice at Doctor's Office; the patients had a rhinitis and irritated eyes; the condition had been unchanged during the last 2 weeks (no treatment was received during this period). The patient received the ImmuMax-treatment as described in example 1 and was asked to report after 5 days and to fill out the questionnaire in the patient's diary. The total symptom score had been reduced >95% during the first 2–3 days of treatment.

Case 2

A 38-year old patient (CH/120962) who was notoriously allergic to birch pollen went to her Doctor's Office seek help; the exacerbations included rhinits and irritated eyes; the symptoms had lasted for 2–3 days; no treatment was initiated at the time the patient went to Doctor's Office. The patient received the same treatment as in case 1 and was asked to fill in patients diary and reported back 5 days later: The initial patient score was very high for hoarseness, sore throat and scratchy throat, coughs; etc. After 2 days treatment with ImmuMaX a significant improvement was noted as the symptom score decreased >75%.

Case 3

A 66-year old patient (ES/270334) had developed common cold symptoms which had sustained for 2 weeks; she received ImmuMaX as described above and reported back 5 days later: at day 0, the symptom score was approx. 50% of the total possible score; the symptom score was reduced >95% after 2–3 days of treatment.

Preliminary Conclusion

Based on the results from this very limited group of allergic patients it seems as if, Venoruton® has a certain effect vs. allergy (pollen allergy and the like); furthermore, allergy which may have been induced via a slow upper airway infection (viral or bacterial or both) may also lend itself to an efficient treatment using the ImmuMax.

Commentary

The fact treatment was given exclusively by the oral/local route also deserves further exploitations as this manner of administration is rather surprising giving the fact that most if not all treatments vs. allergic conditions are given either as spray or systemically. Our new administration form support the notion that one of the very early events initiating allergic reactions/asthma like syndromes could be the recruitment of the neutrophile granulocytes which as a matter of fact is in constant contact with the areas affected by infectious processes and/or inflammatory responses which in turn lend support to our current hypothesis namely, that it may be possible to control these events via drugs as Troxerutin or the like.

Example 7

Preliminary Trial Involving 7 Common Cold Patients at Doctors Office Treated with ImmuMaxZn 7 patients reporting at the Doctor's office, who had experienced the usual symptoms of common cold (sore throat, coughing, sneezing, running nose etc.) for 1–3 days, were treated. Each patient received 20 ImmuMaxZn tablets (containing 50 mg veneruton and 50 mg ZnGluconate, see preparation C) orally in the course of a 3 day treatment. On the first day patients received 5–7 tablets. Patients were asked to keep a patient's diary (see herein above). 7 out of 7 patients responded to the treatment with a 40–50% reduction in symptom score based on the patient diaries.

The results are shown in FIG. 6 and table 9. The curve demonstrates a marked decrease in symptom score after treatment. The reduction in symptom score made it possible for the patients to attend their normal duties.

Example 8

Trial Including 42 Patients Cuffering from Common Cold

The trial was performed in Denmark, only adults participated in the trial. 42 'patients suffering from' common cold were treated with either Immumax (preparation A) or ImmumaxZn (preparation C). Each patient received a maximum of 5 lozenges daily and a total of 20 lozenges during the course of treatment. Each lozenge was administrated by placing it under/on the tongue and allowing it to dissolve slowly (3–5 min.) and the following 10 min. the patient did not drink or eat.

Each patient was asked to fill in the patients diary (see herein above). The results of the trial is summarised in table 10 to 17.

There is a significant decrease in symptom score after 3 days of treatment with either Immumax or ImmumaxZn. However, when comparing the results of table 11 and table 15 it becomes clear that patients suffering from a typical common cold syndrome who started treatment within 3 days after the onset of the symptoms respond better to treatment with ImmuMaxZn than to treatment with ImmuMax. A mean reduction in symptom score of 59% after 3 days treatment With ImmuMax is observed, but 78% mean reduction in symptom score after 3 days treatment with ImmuMaxZn is observed.

Furthermore, it appears that the success of treatment is not dependent on the month in which the treatment was undertaken. Since the majority of common colds in Denmark occuring in September, October and November are caused by rhinovirus and the majority of common colds occuring in Denmark in January, February and March are caused by coronaviruses, this indicates that the treatment is effective against different kinds of virus infections. Accordingly, it is likely that the effect of ImmuMax or ImmuMaxZn is not a direct antiviral effect in vivo.

TABLE 10

Patients with a typical common cold syndrome presented within 24 h treated with ImmuMaxZn

| Month | Pt. No. | Days of Symptoms | Initial SS | SS on Day 3 | Cured (C or NC) | Allergen | Patient's Remark |
|---|---|---|---|---|---|---|---|
| Nov | 21-00 | <1 | 14 | 2 | C | No | |
| March | 12-01 | <1 | 6 | 0 | C | No | Good effect |

TABLE 11

Patients with a typical common cold syndrome presented within 3 days treated with ImmuMaxZn

| Month | Pt. No. | Days of Symptoms | Initial SS | SS on Day 3 | Cured (C or NC) | Allergen | Patient's Remark |
|---|---|---|---|---|---|---|---|
| Nov. | 22-00 | 3 | 11 | 4 | C | No | |
| Nov. | 27-00 | 3 | 14 | 0 | C | No | Very good |
| Nov. | 37-00 | 1 | 10 | 0 | C | No | good |
| Dec. | 41-00 | 3 | 30 | 3 | C | No | |
| Dec. | 42-00 | 1 | 10 | 7 | Partial | No | Good ! |
| Jan. | 03-01 | 2 | 24 | 6 | Partial | No | Good effect ! |
| March | 07-01 | 2 | 18 | 6 | Partial | No | |

TABLE 12

Patients with common cold syndrome/allergy treated with ImmuMaxZn

| Month | Pt. No. | Days of Symptoms | Initial SS | SS on Day 3 | Cured (C or NC) | Allergen | Patient's Remark |
|---|---|---|---|---|---|---|---|
| Nov. | 29-00 | 3 | 15 | 3 | C | Pollen | Average |
| Nov. | 31-00 | 14 | 10 | 5 | (C) | Birch | |
| Nov. | 35-00 | 8 | 20 | 14 | NC | | |
| Dec. | 46-00 | 3 | 10 | 2 | C | Grass | Good |
| Dec. | 47-00 | 3 | 20 | 15 | NC | Grass | |
| March | 08-01 | 2 | 16 | 5 | (C) | Pollen | Good |

TABLE 13

Patients (without any allergic background) with a typical common cold syndrome presented after 3 days treated with ImmuMaxZn

| Month | Pt. No. | Days of Symptoms | Initial SS | SS on Day 3 | Cured (C or NC) | Allergen | Patient's Remark |
|---|---|---|---|---|---|---|---|
| Nov. | 28-00 | 6 | 21 | 9 | PR | No | |
| Nov. | 33-00 | 30 | 5 | 5 | NC | No | |
| Nov. | 34-00 | 4–5 | 29 | 29 | NC | No | |
| Nov. | 36-00 | 64 | 22 | 23 | NC | No | |
| Jan. | 48-00 | 6 | 9 | 2 | C | No | |
| March | 06-01 | 7 | 11 | 2 | C | No | Good effect |
| March | 09-01 | 14 | 7 | 3 | C | No | Good effect |

TABLE 14

Patients with a typical common cold syndrome presented within 24 h treated with ImmuMax

| Month | Pt. No. | Days of Symptoms | Initial SS | SS on Day 3 | Cured (C or NC) | Allergen | Patient's Remark |
|---|---|---|---|---|---|---|---|
| Oct. | 17-00 | <1 | 18 | 21 | NC | No | |
| Nov. | 30-01 | <1 | 5 | 5 | NC | No | |

TABLE 15

Patients with a typical common cold syndrome presented within 3 days treated with ImmuMax

| Month | Pt. No. | Days of Symptoms | Initial SS | SS on Day 3 | Cured (C) Or NC | Allergen | Patient's Remark |
|---|---|---|---|---|---|---|---|
| Jan. | 13-00 | 2 | 20 | 1 | C | No | |
| Oct. | 14-00 | 2 | 33 | 2 | C | No | |
| Nov. | 15-00 | 2 | 11 | 9 | NC | No | |
| Dec. | 19-00 | 2 | 32 | 30 | NC | No | |
| Nov. | 20-00 | 2 | 23 | 9 | Partial | No | |
| Nov. | 38-00 | 3 | 9 | 3 | C | No | good |
| March | 07-01 | 2 | 18 | 6 | Partial | No | |

TABLE 16

Patients with common cold syndrome/allergy treated with ImmuMax

| Month | Pt. No. | Days of Symptoms | Initial SS | SS on Day 3 | Cured (C) Or NC | Allergen | Patient's Remark |
|---|---|---|---|---|---|---|---|
| Nov. | 02-00 | 14 | 27 | 8 | (C) | | |
| Nov. | 03-00 | 14 | 5 | 0 | C | | |
| Jan. | 52-00 | 6 | 15 | 12 | NC | grass | |
| Jan. | 53-00 | 6 | 10 | 7 | NC | grass | week |

TABLE 17

Patients (without any allergic background) with a typical common cold syndrome presented after 3 days treated with ImmuMax

| Month | Pt. No. | Days of Symptoms | Initial SS | SS on Day 3 | Cured (C) Or NC | Allergen | Patient's Remark |
|---|---|---|---|---|---|---|---|
| Jan. | 18-00 | 4 | 33 | 2 | C | no | good |
| March | 25-00 | 14 | 15 | 1 | C | no | |
| Dec. | 39-00 | 8 | 15 | 3 | C | no | average |
| Dec. | 40-00 | 6 | 17 | 5 | C | no | average |
| Dec. | 43-00 | 30 | 9 | 7 | NC | no | |
| Jan. | 18-00 | 4 | 33 | 2 | C | no | good |
| March | 25-00 | 14 | 15 | 1 | C | no | |

Table 10 to 17. SS symptom score, C cured, NC not cured, Pt. No. patient number, month indicates the month in which the treatment was performed, Days of symptom indicates the number of days the patient was suffering from common cold or a common cold related condition prior to the onset of treatment. Day 3 is day 3 of treatment.

REFERENCES

Arruda, E., et al., Location of human rhinovirus replication in the upper respiratory tract by in situ hybridization. J. Inf. Dis. —JID, 1995. 171 (May): p. 1329–1333.

Berg, K., Simonsen, B. H., Hansen, M. B., and Nielsen, S., 1989, A Method for Analysing a sample for the presence of a biological substance, especially a virus, use of the method for quantitative determination of biological substances and agents for use in as we as novel substances detected by the method, PCT/DK/, 89/00010, pp. 1.

Berg, K., Hansen, M. B., and Nielsen, S. E., 1990, A sensitive bioassay for presice quantification of interferon activity as measured via the mitichondrial dehydrogenase function in cells (MTT-method), AMPIS, 98, 156.

Berg, K., and Owen, T. C., 2001 a, The usage of the MTS(PMS-method as a tool for measurements of rhinovirus infections in vitro and its application for quantification of antiviral activity, J. APMIS, (submitted).

Broide, D. H. et al.: J. Allergy Clin. Immunol. 89:958 (1992).

Cate, T., R. B. Couch, and K. M. Johnson, Studies with rhinoviruses in volunteers: production of illness, effects of naturally acquired antibody and demonstration of a protective effect not associated with serum antibody. J. Clin. Invest., 1964. 43(no. 1): p. 56–67.

Cate, T. R., G. Douglas, and R. B. Couch, Interferon and resistance to upper respiratory virus illness. Proc. Soc. Exp. Biol. Med., 1969. 131: p. 631–636.

Farr, B., et al., A method for measuring polymorphonuclear leukocyte concentration in nasal mucus. Acta Otolaryngol (Stockh), 1984. suppl. 413: p. 15–18.

Fachet, F. and M. Gabor, Effect of flavonoids on delayed-type hypersensitivity in inbred mice. Flavonoids . . . , ed. F.e. al. 1977. 395–399.

W. Felix, The actions of hydroxyethylrutoside on edema formation due to various capillary damaging substances. Flavonoids and Bioflavonoids, ed. F.e. al. 1977: Elvier. 411–416.

Gabor, M. and G. Blazso, Effect of o-beta-hydroxyethyl-rutin on rat-paw eodema induced by carrageenin and prostaglandin E1. Flavonoids . . . , ed. F.e. al. 1977: Elsvier. 38186.

Gaffey, M. and e. al, Ipratropium bromide treatment of experimental rhirovirus infection. Antimicrob. Agents Chemother., 1988. 32: p. 1644–1647.

Gem, J. E., et al., Rhinovirus enters but does not replicate inside monocytes and airway macrophages. J. Immunol., 1996.: p. 621–627.

Gem, J. E. and W. W. Busse, Association of rhinovirus infections with asthma. Clinical Microbiology Reviews, 1999. 12 (no. 1, January): p. 9–18.

Ginsburg, I., *Could synergistic interactions among reactive oxygen species, proteinases, membrane-perforating enzymes, hydrolases, microbial hemolysins and cytokines be the main cause of tissue damage in infectious and inflammatory conditions?* Med. Hypotheses, 1998. 51(4): p. 337–46

Graham, N., et al., Adverse effects of aspirin, acetaminophen and ibuprophen on immune function, viral shedding and clinical status in rhinovirus-infected volunteers. J. Infect. Dis., 1990. 162: p. 1277–1282.

Grünberg, K. and P. J. Sterk, Rhinovirus. infections: induction and modulation of airways inflammation in asthma. Clinical and Experimental Allergy, 1999. 29(suppl. 2): p. 65–73.

Gwaltney, J. M. j., Rhinovirus infection of the normal human airway. Review american journal of respiratoty and critical care medicine, 1995. 152(4): p. S36–S39.

Hansen, M. B., Nielsen, S. E., and Berg, K., 1989, Re-examination and futher development of a precise and rapid dye method for measuring cell growth/cell kill, J. Immunol.Methods, 119, 203.

Hayden, F. G., et al., Human nasal mucosal responses to topically applied recombinant leukocyte A interferon. The journal of infectious diseases, 1987. 156(1): p. 64–72.

Hayden, f., J. J. Gwaltney, and R. Colonno, Modification of experimental rhinovirus colds by receptor blockade. Antiviral Res., 1988. 9: p. 233–247.

Ihrcke, N. S., et al., Role of heparan sulfate in immune system-blood vessel interactions. Review. Immunology today, 1993. 14(10): p. 500–505.

Jackson et al., Arch. Internal. Med. 101:267–278,1958

Johnston, S. L., et al., Use of polymerase chain reaction for diagnosis of picornavirus infection in subjects with and without respiratory symptoms. Journal of clinical microbiology., 1993. Jan.: p. 111–117.

Monto, A. and e. al, Ineffectiveness of postexposure prophylaxis of rhinovirus infection with low dose intranasal alpha 2b interferon in families. Antimicrobiol. Agents Chemother., 1989. 33: p. 387–390.

Mussad S B, Macknin M L, Medendorp S V nad Mason P, 1996, Zinc gluconate lozenges for testing the common cold, a randomised, double blind, placebo-controlled study.

Naclerio, R. and et al, Kinins are generated during experimental rhinovirus colds. J, Infect. Dis., 1988. 157: p. 133–142.

Proud, D. and et al, Kinins are generated in nasal secretions during natural rhinovirus colds. J. Infect. Dis., 1990. 161: p. 120–123.

Rotbart, H. A., *Antiviral therapy for interoviruses and rhinoviruses*. Antiviral Chemistry & Chemotherapy, 2000. 11: p. 261–271.

Spector, S. L., The commen cold: current therapy and natural history. J. allergy. clin immunol., 1995. 95(5 part 2): p. 1133–1138.

Sperber, S. P., P. Levine, and e. al, Ineffectivness of recombinant interferon-beta-serine nasal drops for prophylaxis of natural colds. J. Infect. Dis., 1989. 160: p. 700–705.

Tumer, R. B., et al., Sites of virus recovery and antigen detection in epithelial cells during experimental rhinovirus infection. Acta Otolaryngol (Stockh), 1984. suppl. 413: p. 9–14.

Van Damme, J., et al., A novel. NH2-terminal sequence-characterized human monokine possessing neutrophil chemotactic, skin-reactive, and granulocytosis-promoting activity. J. exp. med., 1988. 4: p. 1364–1376.

Winther, B., et al., Study of bacteria in the nasal cavity and nasopharynx during naturally acquired common colds. Acta otolaryng., 1984. 98: p. 315–320.

Winther, B., et al., Light and scanning electron microscopy of nasal biopsy material from patients with naturel acquired common colds. Acta otolaryng., 1984. 97: p. 309–318.

Winther, B., et al., Histopathological examination and enumeration of polymorphonuclea leukocytes in the nasal mucosa during experimental rhinovirus colds. Acta otolaryng.supp., 1984. 413: p. 19–24.

Winther, B., et al., Intranasal spread of rhinovirus during point-inoculation of the nasal mucosa. Jpn. JAMA, 1987. 5: p. 99–103.

Winther, B., et al., Lymphocyte subsets in normal airway of the human nose. Arch. otosryng. head neck surg., 1987. 113: p. 59–62.

Winther, B., Effects on the nasal mucosa of upper resiratory viruses (common cold), 1993, University of Copenhagen.

Winther, B., Effects on the nasal mucosa of upper respiratory viruses (common cold). Laegeforeningens Forlag, 1993

Winther, B., et al., Viral-induced rhinitis. Am. J. Rhinology, 1998. 12(no. 1, January–February): p. 17–20.

The invention claimed is:

1. A method of treatment of symptoms selected from the group consisting of cough, sneezing, muscle pain, sore throat, hoarseness, headache, malaise, chilliness, nasal discharge, nasal obstruction, pain relating to the sinuses, rhinitis, swelling of mucosal membranes, pharyngitis and bronchitis, comprising administering to an individual in need thereof a therapeutically effective dosage of a pharmaceutically acceptable composition comprising at least one flavonoid which is a hydroxyethylrutoside, or a salt thereof.

2. The method according to claim 1 wherein the pharmaceutical composition does not comprise any vitamin.

3. The method according to claim 1 wherein at least one flavonoid is troxerutin of the formula:

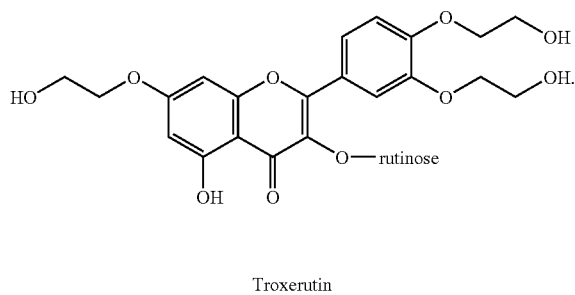

Troxerutin

4. The method according to claim 1, wherein said composition comprises mono-, di-, tri- and tetrahydroxyethyl rutosides.

5. The method according to claim 1, wherein the treatment is in combination with a second treatment, wherein the second treatment comprises administration of a therapeutic agent selected from the group consisting of oseltamivir phosphate, pleconaril, interferons, and rimantadine.

6. The method according to claim 1, wherein the treatment is in combination with a second treatment, wherein the second treatment comprises administration of a pharmaceutically acceptable $Zn^{2+}$ salt and/or complex.

7. The method of claim 1 wherein said composition further comprises a pharmaceutically acceptable metal complex.

8. The method of claim 1 in which said individual is suffering from common cold.

9. The method of claim 1 in which said individual is suffering from a viral infection of the upper and/or lower respiratory tract, and/or eyes.

10. The method according to claim 9, wherein the viral infection is caused by one or more viruses selected from the group consisting of adenoviruses, parvoviruses, picornaviruses, reoviruses, orthomyxoviruses, paramyxoviruses, arenaviruses, caliciviruses, coronaviruses, rhinovirus, influenza virus, echovirus, respiratory syncytial virus (RSV) and coxsackie virus.

11. The method according to claim 9, wherein the infection is caused by one or more viruses selected from the group consisting of coronaviruses and rhinoviruses.

12. The method according to claim 10, wherein the influenza virus is selected from the group consisting of influenza virus type A and influenza virus type B.

13. The method of claim 1 in which said individual is suffering from a bacterial infection of the upper and/or lower respiratory tract, and/or eyes.

14. The method of claim 1 in which said individual is suffering from rhinitis.

15. The method of claim 1 in which said individual is suffering from hay fever.

16. The method of claim 9 in which the viral infection is secondary to the common cold.

17. The method of claim 13 in which the bacterial infection is secondary to the common cold.

18. A method of treating rhinitis or hay fever which comprises administering to an individual in need thereof a therapeutically effective dosage of a pharmaceutically acceptable composition comprising at least one flavonoid which is a hydroxyethylrutoside, or a salt thereof.

19. A method of treating common cold which comprises administering to an individual in need thereof a therapeutically effective dosage of a pharmaceutically acceptable composition comprising at least one flavonoid which is a hydroxyethylrutoside, or a salt thereof.

20. The method of claim 1 in which at least one of said symptoms is attributable, at least in part, to a common cold.

21. The method of claim 3 in which said individual is suffering from common cold.

22. The method of claim 4 in which said individual is suffering from common cold.

23. The method of claim 6 in which said individual is suffering from common cold.

24. The method of claim 7 in which said individual is suffering from common cold.

25. The method of claim 3 in which at least one of said symptoms is attributable, at least in part, to a common cold.

26. The method of claim 4 in which at least one of said symptoms is attributable, at least in part, to a common cold.

27. The method of claim 6 in which at least one of said symptoms is attributable, at least in part, to a common cold.

28. The method of claim 7 in which at least one of said symptoms is attributable, at least in part, to a common cold.

29. The method according to claim 9 wherein at least one flavonoid is troxerutin.

30. The method according to claim 13 wherein at least one flavonoid is troxerutin.

* * * * *